(12) United States Patent
Miller et al.

(10) Patent No.: US 11,986,409 B2
(45) Date of Patent: May 21, 2024

(54) STENT DELIVERY UNDER DIRECT VISUALIZATION

(71) Applicant: INTUITIVE SURGICAL OPERATIONS, INC., Sunnyvale, CA (US)

(72) Inventors: David Miller, Boulder, CO (US); Ruey-Feng Peh, Singapore (SG); Vahid Saadat, Atherton, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 61 days.

(21) Appl. No.: 17/569,193

(22) Filed: Jan. 5, 2022

(65) Prior Publication Data

US 2022/0125611 A1    Apr. 28, 2022

Related U.S. Application Data

(60) Continuation of application No. 16/359,447, filed on Mar. 20, 2019, now Pat. No. 11,241,325, which is a
(Continued)

(51) Int. Cl.
*A61F 2/958* (2013.01)
*A61B 1/00* (2006.01)
(Continued)

(52) U.S. Cl.
CPC .......... *A61F 2/958* (2013.01); *A61B 1/00089* (2013.01); *A61B 1/044* (2022.02);
(Continued)

(58) Field of Classification Search
CPC .............. A61F 2/958; A61F 2250/0039; A61F 2002/821; A61B 34/20
See application file for complete search history.

(56) References Cited

U.S. PATENT DOCUMENTS

| | | |
|---|---|---|
| 623,022 A | 4/1899 | Johnson |
| 2,305,462 A | 12/1942 | Wolf |

(Continued)

FOREIGN PATENT DOCUMENTS

| | | |
|---|---|---|
| DE | 10028155 A1 | 12/2000 |
| EP | 0283661 A2 | 9/1988 |

(Continued)

OTHER PUBLICATIONS

Avitall B., et al., "Right-Sided Driven Atrial Fibrillation in a Sterile Pericarditis Dog Model," Pacing and Clinical Electrophysiology, 1994, vol. 17, pp. 774.
(Continued)

*Primary Examiner* — Tuan V Nguyen
(74) *Attorney, Agent, or Firm* — Haynes & Boone, LLP.

(57) ABSTRACT

A system includes a deployment catheter having a lumen, a delivery sheath configured for positioning within the lumen of the deployment catheter, and a first measurement instrument configured for positioning within the delivery sheath. The first measurement instrument includes a plurality of expandable members each having a known diameter in an expanded state. The first measurement instrument is configured to determine a diameter of an anatomical lumen based on the known diameter of a most proximal expandable member that fits within the anatomical lumen.

19 Claims, 12 Drawing Sheets

Related U.S. Application Data division of application No. 14/490,107, filed on Sep. 18, 2014, now Pat. No. 10,278,849, which is a continuation of application No. 12/367,019, filed on Feb. 6, 2009, now Pat. No. 8,858,609.

(60) Provisional application No. 61/026,795, filed on Feb. 7, 2008.

(51) Int. Cl.
*A61B 1/04* (2006.01)
*A61B 1/12* (2006.01)
*A61B 34/20* (2016.01)
*A61F 2/82* (2013.01)

(52) U.S. Cl.
CPC ............... *A61B 1/12* (2013.01); *A61B 34/20* (2016.02); *A61F 2002/821* (2013.01); *A61F 2250/0039* (2013.01)

(56) References Cited

U.S. PATENT DOCUMENTS

| | | | |
|---|---|---|---|
| 2,453,862 A | 11/1948 | Salisbury | |
| 3,559,651 A | 2/1971 | Moss | |
| 3,661,148 A | 5/1972 | Kolin | |
| 3,874,388 A | 4/1975 | King et al. | |
| 4,175,545 A | 11/1979 | Termanini | |
| 4,326,529 A | 4/1982 | Doss et al. | |
| 4,445,892 A | 5/1984 | Hussein et al. | |
| 4,470,407 A | 9/1984 | Hussein | |
| 4,517,976 A | 5/1985 | Murakoshi et al. | |
| 4,569,335 A | 2/1986 | Tsuno | |
| 4,576,146 A | 3/1986 | Kawazoe et al. | |
| 4,615,333 A | 10/1986 | Taguchi | |
| 4,619,247 A | 10/1986 | Inoue et al. | |
| 4,676,258 A | 6/1987 | Inokuchi et al. | |
| 4,681,093 A | 7/1987 | Ono et al. | |
| 4,709,698 A | 12/1987 | Johnston et al. | |
| 4,710,192 A | 12/1987 | Liotta et al. | |
| 4,727,418 A | 2/1988 | Kato et al. | |
| 4,784,133 A | 11/1988 | Mackin | |
| 4,848,323 A | 7/1989 | Marijnissen et al. | |
| 4,911,148 A | 3/1990 | Sosnowski et al. | |
| 4,914,521 A | 4/1990 | Adair | |
| 4,943,290 A | 7/1990 | Rexroth et al. | |
| 4,950,285 A | 8/1990 | Wilk | |
| 4,957,484 A | 9/1990 | Murtfeldt | |
| 4,961,738 A | 10/1990 | Mackin | |
| 4,976,710 A | 12/1990 | Mackin | |
| 4,991,578 A | 2/1991 | Cohen | |
| 4,994,069 A | 2/1991 | Ritchart et al. | |
| 4,998,916 A | 3/1991 | Hammerslag et al. | |
| 4,998,972 A | 3/1991 | Chin et al. | |
| 5,047,028 A | 9/1991 | Qian | |
| 5,057,106 A | 10/1991 | Kasevich et al. | |
| 5,090,959 A | 2/1992 | Samson et al. | |
| 5,123,428 A | 6/1992 | Schwarz | |
| RE34,002 E | 7/1992 | Adair | |
| 5,156,141 A | 10/1992 | Krebs et al. | |
| 5,171,259 A | 12/1992 | Inoue | |
| 5,281,238 A | 1/1994 | Chin et al. | |
| 5,282,827 A | 2/1994 | Kensey et al. | |
| 5,306,234 A | 4/1994 | Johnson | |
| 5,313,943 A | 5/1994 | Houser et al. | |
| 5,320,605 A * | 6/1994 | Sahota | A61M 25/1011 604/101.02 |
| 5,330,496 A | 7/1994 | Alferness | |
| 5,334,159 A | 8/1994 | Turkel | |
| 5,334,193 A | 8/1994 | Nardella | |
| 5,336,252 A | 8/1994 | Cohen | |
| 5,339,800 A | 8/1994 | Wiita et al. | |
| 5,348,554 A | 9/1994 | Imran et al. | |
| 5,353,792 A | 10/1994 | Luebbers et al. | |
| 5,370,647 A | 12/1994 | Graber et al. | |
| 5,373,840 A | 12/1994 | Knighton | |
| 5,375,612 A | 12/1994 | Cottenceau et al. | |
| 5,385,148 A | 1/1995 | Lesh et al. | |
| 5,391,182 A | 2/1995 | Chin | |
| 5,403,326 A | 4/1995 | Harrison et al. | |
| 5,405,376 A | 4/1995 | Mulier et al. | |
| 5,421,338 A | 6/1995 | Crowley et al. | |
| 5,431,649 A | 7/1995 | Mulier et al. | |
| 5,453,785 A | 9/1995 | Lenhardt et al. | |
| 5,462,521 A | 10/1995 | Brucker et al. | |
| 5,471,515 A | 11/1995 | Fossum et al. | |
| 5,498,230 A | 3/1996 | Adair | |
| 5,505,730 A | 4/1996 | Edwards | |
| 5,515,853 A | 5/1996 | Smith et al. | |
| 5,527,338 A | 6/1996 | Purdy | |
| 5,549,603 A | 8/1996 | Feiring | |
| 5,558,619 A | 9/1996 | Kami et al. | |
| 5,571,088 A | 11/1996 | Lennox et al. | |
| 5,575,756 A | 11/1996 | Karasawa et al. | |
| 5,575,810 A | 11/1996 | Swanson et al. | |
| 5,584,872 A | 12/1996 | Lafontaine et al. | |
| 5,591,119 A | 1/1997 | Adair | |
| 5,591,195 A | 1/1997 | Taheri et al. | |
| 5,593,422 A | 1/1997 | Muijs Van De Moer et al. | |
| 5,593,424 A | 1/1997 | Northrup, III | |
| 5,662,671 A | 9/1997 | Barbut et al. | |
| 5,672,153 A | 9/1997 | Lax et al. | |
| 5,676,693 A | 10/1997 | Lafontaine | |
| 5,681,308 A | 10/1997 | Edwards et al. | |
| 5,695,448 A | 12/1997 | Kimura et al. | |
| 5,697,281 A | 12/1997 | Eggers et al. | |
| 5,697,882 A | 12/1997 | Eggers et al. | |
| 5,709,224 A | 1/1998 | Behl et al. | |
| 5,713,907 A | 2/1998 | Hogendijk et al. | |
| 5,713,946 A | 2/1998 | Ben-Haim | |
| 5,716,321 A | 2/1998 | Kerin et al. | |
| 5,722,403 A | 3/1998 | McGee et al. | |
| 5,725,523 A | 3/1998 | Mueller | |
| 5,746,747 A | 5/1998 | McKeating | |
| 5,749,846 A | 5/1998 | Edwards et al. | |
| 5,749,890 A | 5/1998 | Shaknovich | |
| 5,754,313 A | 5/1998 | Pelchy et al. | |
| 5,766,137 A | 6/1998 | Omata | |
| 5,769,846 A | 6/1998 | Edwards et al. | |
| 5,792,045 A | 8/1998 | Adair | |
| 5,797,903 A | 8/1998 | Swanson et al. | |
| 5,823,947 A | 10/1998 | Yoon et al. | |
| 5,827,268 A | 10/1998 | Laufer | |
| 5,829,447 A | 11/1998 | Stevens et al. | |
| 5,842,973 A | 12/1998 | Bullard | |
| 5,843,118 A | 12/1998 | Sepetka et al. | |
| 5,848,969 A | 12/1998 | Panescu et al. | |
| 5,860,974 A | 1/1999 | Abele | |
| 5,860,991 A | 1/1999 | Klein et al. | |
| 5,865,791 A | 2/1999 | Whayne et al. | |
| 5,873,815 A | 2/1999 | Kerin et al. | |
| 5,879,366 A | 3/1999 | Shaw et al. | |
| 5,895,417 A | 4/1999 | Pomeranz et al. | |
| 5,897,487 A | 4/1999 | Ouchi | |
| 5,897,553 A | 4/1999 | Mulier et al. | |
| 5,902,308 A * | 5/1999 | Murphy | A61B 5/1076 600/587 |
| 5,902,328 A | 5/1999 | Lafontaine et al. | |
| 5,904,651 A | 5/1999 | Swanson et al. | |
| 5,908,445 A | 6/1999 | Whayne et al. | |
| 5,925,038 A | 7/1999 | Panescu et al. | |
| 5,928,250 A | 7/1999 | Koike et al. | |
| 5,929,901 A | 7/1999 | Adair et al. | |
| 5,941,845 A | 8/1999 | Tu et al. | |
| 5,944,690 A | 8/1999 | Falwell et al. | |
| 5,964,755 A | 10/1999 | Edwards | |
| 5,968,053 A | 10/1999 | Revelas | |
| 5,971,983 A | 10/1999 | Lesh | |
| 5,986,693 A | 11/1999 | Adair et al. | |
| 5,997,571 A | 12/1999 | Farr et al. | |
| 6,004,269 A | 12/1999 | Crowley et al. | |
| 6,012,457 A | 1/2000 | Lesh | |
| 6,024,740 A | 2/2000 | Lesh et al. | |
| 6,027,501 A | 2/2000 | Goble et al. | |

(56) References Cited

U.S. PATENT DOCUMENTS

| | | | |
|---|---|---|---|
| 6,036,685 A | 3/2000 | Mueller | |
| 6,043,839 A | 3/2000 | Adair et al. | |
| 6,047,218 A | 4/2000 | Whayne et al. | |
| 6,063,077 A | 5/2000 | Schaer | |
| 6,063,081 A | 5/2000 | Mulier et al. | |
| 6,068,653 A | 5/2000 | Lafontaine | |
| 6,071,279 A | 6/2000 | Whayne et al. | |
| 6,071,302 A | 6/2000 | Sinofsky et al. | |
| 6,081,740 A | 6/2000 | Gombrich et al. | |
| 6,086,528 A | 7/2000 | Adair | |
| 6,086,534 A | 7/2000 | Kesten | |
| 6,099,498 A | 8/2000 | Addis | |
| 6,099,514 A | 8/2000 | Sharkey et al. | |
| 6,102,905 A | 8/2000 | Baxter et al. | |
| 6,112,123 A | 8/2000 | Kelleher et al. | |
| 6,115,626 A | 9/2000 | Whayne et al. | |
| 6,123,703 A | 9/2000 | Tu et al. | |
| 6,123,718 A | 9/2000 | Tu et al. | |
| 6,129,724 A | 10/2000 | Fleischman et al. | |
| 6,139,508 A | 10/2000 | Simpson et al. | |
| 6,142,993 A | 11/2000 | Whayne et al. | |
| 6,152,144 A | 11/2000 | Lesh et al. | |
| 6,156,350 A | 12/2000 | Constantz | |
| 6,159,203 A | 12/2000 | Sinofsky | |
| 6,161,543 A | 12/2000 | Cox et al. | |
| 6,164,283 A | 12/2000 | Lesh | |
| 6,167,297 A | 12/2000 | Benaron | |
| 6,168,591 B1 | 1/2001 | Sinofsky | |
| 6,168,594 B1 | 1/2001 | Lafontaine et al. | |
| 6,174,307 B1 | 1/2001 | Daniel et al. | |
| 6,178,346 B1 | 1/2001 | Amundson et al. | |
| 6,190,381 B1 | 2/2001 | Olsen et al. | |
| 6,211,904 B1 | 4/2001 | Adair et al. | |
| 6,224,553 B1 | 5/2001 | Nevo | |
| 6,231,561 B1 | 5/2001 | Frazier et al. | |
| 6,235,044 B1 | 5/2001 | Root et al. | |
| 6,237,605 B1 | 5/2001 | Vaska et al. | |
| 6,238,393 B1 | 5/2001 | Mulier et al. | |
| 6,240,312 B1 | 5/2001 | Alfano et al. | |
| 6,254,598 B1 | 7/2001 | Edwards et al. | |
| 6,258,083 B1 | 7/2001 | Daniel et al. | |
| 6,263,224 B1 | 7/2001 | West | |
| 6,270,492 B1 | 8/2001 | Sinofsky | |
| 6,275,255 B1 | 8/2001 | Adair et al. | |
| 6,290,689 B1 | 9/2001 | Delaney et al. | |
| 6,306,081 B1 | 10/2001 | Ishikawa et al. | |
| 6,310,642 B1 | 10/2001 | Adair et al. | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,315,777 B1 | 11/2001 | Comben | |
| 6,315,778 B1 | 11/2001 | Gambale et al. | |
| 6,322,536 B1 | 11/2001 | Rosengart et al. | |
| 6,325,797 B1 | 12/2001 | Stewart et al. | |
| 6,328,727 B1 | 12/2001 | Frazier et al. | |
| 6,358,247 B1 | 3/2002 | Altman et al. | |
| 6,358,248 B1 | 3/2002 | Mulier et al. | |
| 6,375,654 B1 | 4/2002 | McIntyre | |
| 6,379,345 B1 | 4/2002 | Constantz | |
| 6,385,476 B1 | 5/2002 | Osadchy et al. | |
| 6,387,043 B1 | 5/2002 | Yoon | |
| 6,387,071 B1 | 5/2002 | Constantz | |
| 6,394,096 B1 | 5/2002 | Constantz | |
| 6,396,873 B1 | 5/2002 | Goldstein et al. | |
| 6,398,780 B1 | 6/2002 | Farley et al. | |
| 6,401,719 B1 | 6/2002 | Farley et al. | |
| 6,409,722 B1 | 6/2002 | Hoey et al. | |
| 6,416,511 B1 | 7/2002 | Lesh et al. | |
| 6,419,669 B1 | 7/2002 | Frazier et al. | |
| 6,423,051 B1 | 7/2002 | Kaplan et al. | |
| 6,423,055 B1 | 7/2002 | Farr et al. | |
| 6,423,058 B1 | 7/2002 | Edwards et al. | |
| 6,428,536 B2 | 8/2002 | Panescu et al. | |
| 6,436,118 B1 | 8/2002 | Kayan | |
| 6,440,061 B1 | 8/2002 | Wenner et al. | |
| 6,440,119 B1 | 8/2002 | Nakada et al. | |
| 6,458,151 B1 | 10/2002 | Saltiel | |
| 6,464,697 B1 | 10/2002 | Edwards et al. | |
| 6,474,340 B1 | 11/2002 | Vaska et al. | |
| 6,475,223 B1 | 11/2002 | Werp et al. | |
| 6,478,769 B1 | 11/2002 | Parker | |
| 6,482,162 B1 | 11/2002 | Moore | |
| 6,484,727 B1 | 11/2002 | Vaska et al. | |
| 6,485,489 B2 | 11/2002 | Teirstein et al. | |
| 6,488,653 B1 * | 12/2002 | Lombardo | A61M 25/1002 604/103.06 |
| 6,488,671 B1 | 12/2002 | Constantz et al. | |
| 6,494,902 B2 | 12/2002 | Hoey et al. | |
| 6,497,705 B2 | 12/2002 | Comben | |
| 6,500,174 B1 | 12/2002 | Maguire et al. | |
| 6,502,576 B1 | 1/2003 | Lesh | |
| 6,514,249 B1 | 2/2003 | Maguire et al. | |
| 6,517,533 B1 | 2/2003 | Swaminathan | |
| 6,527,979 B2 | 3/2003 | Constantz et al. | |
| 6,532,380 B1 | 3/2003 | Close et al. | |
| 6,533,767 B2 | 3/2003 | Johansson et al. | |
| 6,537,272 B2 | 3/2003 | Christopherson et al. | |
| 6,540,733 B2 | 4/2003 | Constantz et al. | |
| 6,540,744 B2 | 4/2003 | Hassett et al. | |
| 6,544,195 B2 | 4/2003 | Wilson et al. | |
| 6,547,780 B1 | 4/2003 | Sinofsky | |
| 6,558,375 B1 | 5/2003 | Sinofsky et al. | |
| 6,558,382 B2 | 5/2003 | Jahns et al. | |
| 6,562,020 B1 | 5/2003 | Constantz et al. | |
| 6,572,609 B1 | 6/2003 | Farr et al. | |
| 6,579,285 B2 | 6/2003 | Sinofsky | |
| 6,585,732 B2 | 7/2003 | Mulier et al. | |
| 6,587,709 B2 | 7/2003 | Solf et al. | |
| 6,593,884 B1 | 7/2003 | Gilboa et al. | |
| 6,605,055 B1 | 8/2003 | Sinofsky et al. | |
| 6,613,062 B1 | 9/2003 | Leckrone et al. | |
| 6,622,732 B2 | 9/2003 | Constantz | |
| 6,626,855 B1 | 9/2003 | Weng et al. | |
| 6,626,900 B1 | 9/2003 | Sinofsky et al. | |
| 6,635,070 B2 | 10/2003 | Leeflang et al. | |
| 6,645,202 B1 | 11/2003 | Pless et al. | |
| 6,650,923 B1 | 11/2003 | Lesh et al. | |
| 6,658,279 B2 | 12/2003 | Swanson et al. | |
| 6,659,940 B2 | 12/2003 | Adler | |
| 6,673,090 B2 | 1/2004 | Root et al. | |
| 6,676,656 B2 | 1/2004 | Sinofsky | |
| 6,679,836 B2 | 1/2004 | Couvillon, Jr. et al. | |
| 6,682,526 B1 | 1/2004 | Jones et al. | |
| 6,689,128 B2 | 2/2004 | Sliwa et al. | |
| 6,692,430 B2 | 2/2004 | Adler | |
| 6,701,581 B2 | 3/2004 | Senovich et al. | |
| 6,701,931 B2 | 3/2004 | Sliwa et al. | |
| 6,702,780 B1 | 3/2004 | Gilboa et al. | |
| 6,704,043 B2 | 3/2004 | Goldstein et al. | |
| 6,706,039 B2 | 3/2004 | Mulier et al. | |
| 6,712,798 B2 | 3/2004 | Constantz | |
| 6,719,747 B2 | 4/2004 | Constantz et al. | |
| 6,719,755 B2 | 4/2004 | Sliwa et al. | |
| 6,730,063 B2 | 5/2004 | Delaney et al. | |
| 6,736,810 B2 | 5/2004 | Hoey et al. | |
| 6,751,492 B2 | 6/2004 | Ben-Haim | |
| 6,755,790 B2 | 6/2004 | Stewart et al. | |
| 6,755,811 B1 | 6/2004 | Constantz | |
| 6,764,487 B2 | 7/2004 | Mulier et al. | |
| 6,771,996 B2 | 8/2004 | Bowe et al. | |
| 6,773,402 B2 | 8/2004 | Govari et al. | |
| 6,780,151 B2 | 8/2004 | Grabover et al. | |
| 6,805,128 B1 | 10/2004 | Pless et al. | |
| 6,805,129 B1 | 10/2004 | Pless et al. | |
| 6,811,562 B1 | 11/2004 | Pless | |
| 6,833,814 B2 | 12/2004 | Gilboa et al. | |
| 6,840,923 B1 | 1/2005 | Lapcevic | |
| 6,840,936 B2 | 1/2005 | Sliwa et al. | |
| 6,849,073 B2 | 2/2005 | Hoey et al. | |
| 6,858,005 B2 | 2/2005 | Ohline et al. | |
| 6,858,026 B2 | 2/2005 | Sliwa et al. | |
| 6,863,668 B2 | 3/2005 | Gillespie et al. | |
| 6,866,651 B2 | 3/2005 | Constantz | |
| 6,887,237 B2 | 5/2005 | McGaffigan | |

(56) References Cited

U.S. PATENT DOCUMENTS

| | | |
|---|---|---|
| 6,892,091 B1 | 5/2005 | Ben-Haim et al. |
| 6,896,690 B1 | 5/2005 | Lambrecht et al. |
| 6,899,672 B2 | 5/2005 | Chin et al. |
| 6,915,154 B1 | 7/2005 | Docherty et al. |
| 6,916,284 B2 | 7/2005 | Moriyama |
| 6,923,805 B1 | 8/2005 | Lafontaine et al. |
| 6,929,010 B2 | 8/2005 | Vaska et al. |
| 6,932,809 B2 | 8/2005 | Sinofsky |
| 6,939,348 B2 | 9/2005 | Malecki et al. |
| 6,942,657 B2 | 9/2005 | Sinofsky et al. |
| 6,949,095 B2 | 9/2005 | Vaska et al. |
| 6,953,457 B2 | 10/2005 | Farr et al. |
| 6,955,173 B2 | 10/2005 | Lesh |
| 6,962,589 B2 | 11/2005 | Mulier et al. |
| 6,971,394 B2 | 12/2005 | Sliwa et al. |
| 6,974,464 B2 | 12/2005 | Quijano et al. |
| 6,979,290 B2 | 12/2005 | Mourlas et al. |
| 6,982,740 B2 | 1/2006 | Adair et al. |
| 6,984,232 B2 | 1/2006 | Vanney et al. |
| 6,994,094 B2 | 2/2006 | Schwartz |
| 7,019,610 B2 | 3/2006 | Creighton et al. |
| 7,025,746 B2 | 4/2006 | Tal |
| 7,030,904 B2 | 4/2006 | Adair et al. |
| 7,041,098 B2 | 5/2006 | Farley et al. |
| 7,042,487 B2 | 5/2006 | Nakashima |
| 7,044,135 B2 | 5/2006 | Lesh |
| 7,052,493 B2 | 5/2006 | Vaska et al. |
| 7,090,683 B2 | 8/2006 | Brock et al. |
| 7,090,688 B2 | 8/2006 | Nishtala et al. |
| 7,118,566 B2 | 10/2006 | Jahns |
| 7,156,845 B2 | 1/2007 | Mulier et al. |
| 7,163,534 B2 | 1/2007 | Brucker et al. |
| 7,166,537 B2 | 1/2007 | Jacobsen et al. |
| 7,169,144 B2 | 1/2007 | Hoey et al. |
| 7,186,214 B2 | 3/2007 | Ness |
| 7,207,984 B2 | 4/2007 | Farr et al. |
| 7,217,268 B2 | 5/2007 | Eggers et al. |
| 7,242,832 B2 | 7/2007 | Carlin et al. |
| 7,247,155 B2 | 7/2007 | Hoey et al. |
| 7,261,711 B2 | 8/2007 | Mulier et al. |
| 7,263,397 B2 | 8/2007 | Hauck et al. |
| 7,276,061 B2 | 10/2007 | Schaer et al. |
| 7,309,328 B2 | 12/2007 | Kaplan et al. |
| 7,416,552 B2 | 8/2008 | Paul et al. |
| 7,435,248 B2 | 10/2008 | Taimisto et al. |
| 7,527,625 B2 | 5/2009 | Knight et al. |
| 7,534,204 B2 | 5/2009 | Starksen et al. |
| 7,569,052 B2 | 8/2009 | Phan et al. |
| 7,637,934 B2 | 12/2009 | Mangiardi et al. |
| 7,651,520 B2 | 1/2010 | Fischell et al. |
| 7,720,528 B2 | 5/2010 | Maschke |
| 7,736,347 B2 | 6/2010 | Kaplan et al. |
| 7,758,499 B2 | 7/2010 | Adler |
| 7,860,555 B2 | 12/2010 | Saadat |
| 7,860,556 B2 | 12/2010 | Saadat |
| 8,078,266 B2 | 12/2011 | Saadat et al. |
| 8,131,350 B2 | 3/2012 | Saadat et al. |
| 8,137,333 B2 | 3/2012 | Saadat et al. |
| 8,690,907 B1 | 4/2014 | Janardhan et al. |
| 8,715,314 B1 | 5/2014 | Janardhan et al. |
| 8,784,434 B2 | 7/2014 | Rosenbluth et al. |
| 8,858,609 B2 | 10/2014 | Miller et al. |
| 9,314,324 B2 | 4/2016 | Janardhan et al. |
| 9,592,068 B2 | 3/2017 | Janardhan et al. |
| 10,278,849 B2 | 5/2019 | Miller et al. |
| 11,241,325 B2 | 2/2022 | Miller et al. |
| 2001/0020126 A1 | 9/2001 | Swanson et al. |
| 2001/0039416 A1 | 11/2001 | Moorman et al. |
| 2001/0047136 A1 | 11/2001 | Domanik et al. |
| 2001/0047184 A1 | 11/2001 | Connors |
| 2002/0004644 A1 | 1/2002 | Koblish |
| 2002/0026145 A1 | 2/2002 | Bagaoisan et al. |
| 2002/0054852 A1 | 5/2002 | Cate |
| 2002/0065455 A1 | 5/2002 | Ben-Haim et al. |
| 2002/0077564 A1 | 6/2002 | Campbell et al. |
| 2002/0077647 A1 | 6/2002 | Snow et al. |
| 2002/0087169 A1 | 7/2002 | Brock et al. |
| 2002/0091304 A1 | 7/2002 | Ogura et al. |
| 2002/0138088 A1 | 9/2002 | Nash et al. |
| 2002/0147458 A1 | 10/2002 | Hiblar et al. |
| 2002/0165574 A1 | 11/2002 | Ressemann et al. |
| 2002/0165598 A1 | 11/2002 | Wahr et al. |
| 2002/0169377 A1 | 11/2002 | Khairkhahan et al. |
| 2003/0009085 A1 | 1/2003 | Arai et al. |
| 2003/0035156 A1 | 2/2003 | Cooper |
| 2003/0036698 A1 | 2/2003 | Kohler et al. |
| 2003/0069593 A1 | 4/2003 | Tremulis et al. |
| 2003/0120142 A1 | 6/2003 | Dubuc et al. |
| 2003/0130572 A1 | 7/2003 | Phan et al. |
| 2003/0144657 A1 | 7/2003 | Bowe et al. |
| 2003/0171741 A1 | 9/2003 | Ziebol et al. |
| 2003/0181939 A1 | 9/2003 | Bonutti |
| 2003/0208222 A1 | 11/2003 | Zadno-Azizi |
| 2003/0212394 A1 | 11/2003 | Pearson et al. |
| 2003/0220574 A1 | 11/2003 | Markus et al. |
| 2003/0222325 A1 | 12/2003 | Jacobsen et al. |
| 2004/0049211 A1 | 3/2004 | Tremulis et al. |
| 2004/0054335 A1 | 3/2004 | Lesh et al. |
| 2004/0054389 A1 | 3/2004 | Osypka |
| 2004/0082833 A1 | 4/2004 | Adler et al. |
| 2004/0093056 A1 | 5/2004 | Johnson et al. |
| 2004/0117032 A1 | 6/2004 | Roth |
| 2004/0133113 A1 | 7/2004 | Krishnan |
| 2004/0138707 A1 | 7/2004 | Greenhalgh |
| 2004/0147806 A1 | 7/2004 | Adler |
| 2004/0147852 A1 | 7/2004 | Brister et al. |
| 2004/0147911 A1 | 7/2004 | Sinofsky |
| 2004/0147912 A1 | 7/2004 | Sinofsky |
| 2004/0147913 A1 | 7/2004 | Sinofsky |
| 2004/0158143 A1 | 8/2004 | Flaherty et al. |
| 2004/0158289 A1 | 8/2004 | Girouard et al. |
| 2004/0167503 A1 | 8/2004 | Sinofsky |
| 2004/0181237 A1 | 9/2004 | Forde et al. |
| 2004/0199052 A1 | 10/2004 | Banik et al. |
| 2004/0210239 A1 | 10/2004 | Nash et al. |
| 2004/0215180 A1 | 10/2004 | Starkebaum et al. |
| 2004/0220471 A1 | 11/2004 | Schwartz |
| 2004/0230131 A1 | 11/2004 | Kassab et al. |
| 2004/0248837 A1 | 12/2004 | Raz et al. |
| 2004/0249367 A1 | 12/2004 | Saadat et al. |
| 2004/0254523 A1 | 12/2004 | Fitzgerald et al. |
| 2004/0260182 A1 | 12/2004 | Zuluaga et al. |
| 2005/0014995 A1 | 1/2005 | Amundson et al. |
| 2005/0015048 A1 | 1/2005 | Chiu et al. |
| 2005/0020914 A1 | 1/2005 | Amundson et al. |
| 2005/0027163 A1 | 2/2005 | Chin et al. |
| 2005/0038419 A9 | 2/2005 | Arnold et al. |
| 2005/0059862 A1 | 3/2005 | Phan |
| 2005/0059954 A1 | 3/2005 | Constantz |
| 2005/0059965 A1 | 3/2005 | Eberl et al. |
| 2005/0065504 A1 | 3/2005 | Melsky et al. |
| 2005/0090818 A1 | 4/2005 | Pike, Jr. et al. |
| 2005/0096643 A1 | 5/2005 | Brucker et al. |
| 2005/0101984 A1 | 5/2005 | Chanduszko et al. |
| 2005/0107736 A1 | 5/2005 | Landman et al. |
| 2005/0124969 A1 | 6/2005 | Fitzgerald et al. |
| 2005/0131401 A1 | 6/2005 | Malecki et al. |
| 2005/0154252 A1 | 7/2005 | Sharkey et al. |
| 2005/0159702 A1 | 7/2005 | Sekiguchi et al. |
| 2005/0165279 A1 | 7/2005 | Adler et al. |
| 2005/0165391 A1 | 7/2005 | Maguire et al. |
| 2005/0165466 A1 | 7/2005 | Morris et al. |
| 2005/0197530 A1 | 9/2005 | Wallace et al. |
| 2005/0197623 A1 | 9/2005 | Leeflang et al. |
| 2005/0215895 A1 | 9/2005 | Popp et al. |
| 2005/0222554 A1 | 10/2005 | Wallace et al. |
| 2005/0222557 A1 | 10/2005 | Baxter et al. |
| 2005/0222558 A1 | 10/2005 | Baxter et al. |
| 2005/0228417 A1 | 10/2005 | Teitelbaum et al. |
| 2005/0228452 A1 | 10/2005 | Mourlas et al. |
| 2005/0234436 A1 | 10/2005 | Baxter et al. |
| 2005/0234437 A1 | 10/2005 | Baxter et al. |
| 2005/0267328 A1 | 12/2005 | Blumzvig et al. |
| 2005/0278010 A1 | 12/2005 | Richardson |

(56) References Cited

U.S. PATENT DOCUMENTS

| | | |
|---|---|---|
| 2006/0009715 A1 | 1/2006 | Khairkhahan et al. |
| 2006/0009737 A1 | 1/2006 | Whiting et al. |
| 2006/0015096 A1 | 1/2006 | Hauck et al. |
| 2006/0022234 A1 | 2/2006 | Adair et al. |
| 2006/0025651 A1 | 2/2006 | Adler et al. |
| 2006/0025787 A1 | 2/2006 | Morales et al. |
| 2006/0069303 A1 | 3/2006 | Couvillon, Jr. |
| 2006/0074398 A1 | 4/2006 | Whiting et al. |
| 2006/0084839 A1 | 4/2006 | Mourlas et al. |
| 2006/0084945 A1 | 4/2006 | Moll et al. |
| 2006/0085024 A1* | 4/2006 | Pepper ................ A61L 29/085 428/35.9 |
| 2006/0089637 A1 | 4/2006 | Werneth et al. |
| 2006/0111614 A1 | 5/2006 | Saadat et al. |
| 2006/0122587 A1 | 6/2006 | Sharareh |
| 2006/0146172 A1 | 7/2006 | Jacobsen et al. |
| 2006/0149331 A1 | 7/2006 | Mann et al. |
| 2006/0155242 A1 | 7/2006 | Constantz |
| 2006/0161133 A1 | 7/2006 | Laird et al. |
| 2006/0167439 A1 | 7/2006 | Kalser et al. |
| 2006/0183992 A1 | 8/2006 | Kawashima et al. |
| 2006/0217755 A1 | 9/2006 | Eversull et al. |
| 2006/0224167 A1 | 10/2006 | Weisenburgh et al. |
| 2006/0253113 A1 | 11/2006 | Arnold et al. |
| 2006/0258909 A1 | 11/2006 | Saadat et al. |
| 2006/0271032 A1 | 11/2006 | Chin et al. |
| 2007/0005019 A1 | 1/2007 | Okishige |
| 2007/0015964 A1 | 1/2007 | Eversull et al. |
| 2007/0016130 A1 | 1/2007 | Leeflang et al. |
| 2007/0043338 A1 | 2/2007 | Moll et al. |
| 2007/0043413 A1 | 2/2007 | Eversull et al. |
| 2007/0049923 A1 | 3/2007 | Jahns |
| 2007/0055142 A1 | 3/2007 | Webler |
| 2007/0078451 A1 | 4/2007 | Arnold et al. |
| 2007/0083187 A1 | 4/2007 | Eversull et al. |
| 2007/0083217 A1 | 4/2007 | Eversull et al. |
| 2007/0093808 A1 | 4/2007 | Mulier et al. |
| 2007/0100324 A1 | 5/2007 | Tempel et al. |
| 2007/0106146 A1 | 5/2007 | Altmann et al. |
| 2007/0106214 A1 | 5/2007 | Gray et al. |
| 2007/0106287 A1 | 5/2007 | O'Sullivan |
| 2007/0123776 A1 | 5/2007 | Aharoni et al. |
| 2007/0135826 A1 | 6/2007 | Zaver et al. |
| 2007/0167801 A1 | 7/2007 | Webler et al. |
| 2007/0225790 A1 | 9/2007 | Fischell et al. |
| 2007/0265609 A1 | 11/2007 | Thapliyal et al. |
| 2007/0265610 A1 | 11/2007 | Thapliyal et al. |
| 2007/0270686 A1 | 11/2007 | Ritter et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0009859 A1 | 1/2008 | Auth et al. |
| 2008/0015563 A1 | 1/2008 | Hoey et al. |
| 2008/0015569 A1 | 1/2008 | Saadat et al. |
| 2008/0027464 A1 | 1/2008 | Moll et al. |
| 2008/0033241 A1 | 2/2008 | Peh et al. |
| 2008/0057106 A1 | 3/2008 | Erickson et al. |
| 2008/0058590 A1 | 3/2008 | Saadat et al. |
| 2008/0058650 A1 | 3/2008 | Saadat et al. |
| 2008/0058836 A1 | 3/2008 | Moll et al. |
| 2008/0097476 A1 | 4/2008 | Peh et al. |
| 2008/0183081 A1 | 7/2008 | Lys et al. |
| 2008/0214889 A1 | 9/2008 | Saadat et al. |
| 2008/0228032 A1 | 9/2008 | Starksen et al. |
| 2008/0275300 A1 | 11/2008 | Rothe et al. |
| 2008/0281293 A1 | 11/2008 | Peh et al. |
| 2008/0287790 A1 | 11/2008 | Li |
| 2008/0287805 A1 | 11/2008 | Li |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076489 A1 | 3/2009 | Welches et al. |
| 2009/0076498 A1 | 3/2009 | Saadat et al. |
| 2009/0082623 A1 | 3/2009 | Rothe et al. |
| 2009/0112251 A1 | 4/2009 | Qian et al. |
| 2009/0125022 A1 | 5/2009 | Saadat et al. |
| 2009/0143640 A1 | 6/2009 | Saadat et al. |
| 2009/0187074 A1 | 7/2009 | Saadat et al. |
| 2009/0198269 A1 | 8/2009 | Hannes et al. |
| 2009/0221871 A1 | 9/2009 | Peh et al. |
| 2009/0227999 A1 | 9/2009 | Willis et al. |
| 2009/0264727 A1 | 10/2009 | Markowitz et al. |
| 2009/0267773 A1 | 10/2009 | Markowitz et al. |
| 2009/0275799 A1 | 11/2009 | Saadat et al. |
| 2009/0299363 A1 | 12/2009 | Saadat et al. |
| 2009/0306702 A1 | 12/2009 | Miloslavski et al. |
| 2009/0326572 A1 | 12/2009 | Peh et al. |
| 2010/0004506 A1 | 1/2010 | Saadat |
| 2010/0004633 A1 | 1/2010 | Rothe et al. |
| 2010/0004661 A1 | 1/2010 | Verin et al. |
| 2010/0010311 A1 | 1/2010 | Miller et al. |
| 2010/0094081 A1 | 4/2010 | Rothe et al. |
| 2010/0130836 A1 | 5/2010 | Malchano et al. |
| 2011/0060227 A1 | 3/2011 | Saadat |
| 2011/0060298 A1 | 3/2011 | Saadat |
| 2011/0144576 A1 | 6/2011 | Rothe et al. |
| 2012/0016221 A1 | 1/2012 | Saadat et al. |
| 2012/0059366 A1 | 3/2012 | Drews et al. |
| 2019/0216625 A1 | 7/2019 | Miller et al. |

FOREIGN PATENT DOCUMENTS

| | | |
|---|---|---|
| EP | 0301288 A1 | 2/1989 |
| JP | S5993413 A | 5/1984 |
| JP | S59181315 A | 10/1984 |
| JP | H01221133 A | 9/1989 |
| JP | H03284265 A | 12/1991 |
| JP | H05103746 A | 4/1993 |
| JP | H0951897 A | 2/1997 |
| JP | H11299725 A | 11/1999 |
| JP | 2001258822 A | 9/2001 |
| WO | WO-9221292 A2 | 12/1992 |
| WO | WO-9407413 A1 | 4/1994 |
| WO | WO-9503843 A1 | 2/1995 |
| WO | WO-9818388 A1 | 5/1998 |
| WO | WO-03039350 A2 | 5/2003 |
| WO | WO-03053491 A2 | 7/2003 |
| WO | WO-03101287 A2 | 12/2003 |
| WO | WO-2004043272 A1 | 5/2004 |
| WO | WO-2004080508 A2 | 9/2004 |
| WO | WO-2005070330 A1 | 8/2005 |
| WO | WO-2005077435 A1 | 8/2005 |
| WO | WO-2005081202 A1 | 9/2005 |
| WO | WO-2006017517 A2 | 2/2006 |
| WO | WO-2006024015 A1 | 3/2006 |
| WO | WO-2006083794 A2 | 8/2006 |
| WO | WO-2006091597 A1 | 8/2006 |
| WO | WO-2006126979 A2 | 11/2006 |
| WO | WO-2007067323 A2 | 6/2007 |
| WO | WO-2007079268 A2 | 7/2007 |
| WO | WO-2007133845 A2 | 11/2007 |
| WO | WO-2007134258 A2 | 11/2007 |
| WO | WO-2008015625 A2 | 2/2008 |
| WO | WO-2008021994 A2 | 2/2008 |
| WO | WO-2008021997 A2 | 2/2008 |
| WO | WO-2008021998 A2 | 2/2008 |
| WO | WO-2008024261 A2 | 2/2008 |
| WO | WO-2008079828 A2 | 7/2008 |
| WO | WO-2009112262 A2 | 9/2009 |

OTHER PUBLICATIONS

Avitall, et al. "A Catheter System to Ablate Atrial Fibrillation in a Sterile Pericarditis Dog Model," Pacing and Clinical Electrophysiology, 1994, vol. 17, pp. 774.

Avitall, "Vagally Mediated Atrial Fibrillation in a Dog Model can be Ablated by Placing Linear Radiofrequency Lesions at the Junction of the Right Atrial Appendage and the Superior Vena Cava," Pacing and Clinical Electrophysiology, 1995, vol. 18, pp. 857.

Baker B.M., et al., "Nonpharmacologic Approaches to the Treatment of Atrial Fibrillation and Atrial Flutter," Journal of Cardiovascular Electrophysiology, 1995, vol. 6 (10 Pt 2), pp. 972-978.

(56) References Cited

OTHER PUBLICATIONS

Bhakta D., et al., "Principles of Electroanatomic Mapping," Indian Pacing and Electrophysiology Journal, 2008, vol. 8 (1), pp. 32-50.
Bidoggia H., et al., "Transseptal Left Heart Catheterization: Usefulness of the Intracavitary Electrocardiogram in the Localization of the Fossa Ovalis," Cathet Cardiovasc Diagn, 1991, vol. 24 (3), pp. 221-225, PMID: 1764747 [online], [retrieved Feb. 15, 2010]. Retrieved from the Internet: URL: http://www.ncbi.nlm.nih.gov/sites/entrez.
Bredikis J.J., et al., "Surgery of Tachyarrhythmia: Intracardiac Closed Heart Cryoablation," Pacing and Clinical Electrophysiology, 1990, vol. 13 (Part 2), pp. 1980-1984.
Communication from the Examining Division for Application No. EP06734083.6 dated Nov. 12, 2010, 3 pages.
Communication from the Examining Division for Application No. EP06734083.6 dated Oct. 23, 2009, 1 page.
Communication from the Examining Division for Application No. EP08746822.9 dated Jul. 13, 2010, 1 page.
Cox J.L., "Cardiac Surgery for Arrhythmias," Journal of Cardiovascular Electrophysiology, 2004, vol. 15, pp. 250-262.
Cox J.L., et al., "Five-Year Experience With the Maze Procedure for Atrial Fibrillation," The Annals of Thoracic Surgery, 1993, vol. 56, pp. 814-824.
Cox J.L., et al., "Modification of the Maze Procedure for Atrial Flutter and Atrial Fibrillation," The Journal of Thoracic and Cardiovascular Surgery, 1995, vol. 110, pp. 473-484.
Cox J.L., "The Status of Surgery for Cardiac Arrhythmias," Circulation, 1985, vol. 71, pp. 413-417.
Cox J.L., "The Surgical Treatment of Atrial Fibrillation," The Journal of Thoracic and Cardiovascular Surgery, 1991, vol. 101, pp. 584-592.
Elvan A., et al., "Radiofrequency Catheter Ablation of the Atria Reduces Inducibility and Duration of Atrial Fibrillation in Dogs," Circulation, vol. 91, 1995, pp. 2235-2244 [online], [retrieved Feb. 4, 2013]. Retrieved from the Internet: URL: http://circ.ahajournals.org/cgi/content/full/91/8/2235.
Elvan A., et al., "Radiofrequency Catheter Ablation (RFCA) of the Atria Effectively Abolishes Pacing Induced Chronic Atrial Fibrillation," Pacing and Clinical Electrophysiology, 1995, vol. 18, pp. 856.
Elvan, et al., "Replication of the 'Maze' Procedure by Radiofrequency Catheter Ablation Reduces the Ability to Induce Atrial Fibrillation," Pacing and Clinical Electrophysiology, 1994, vol. 17, pp. 774.
European Search Report for Application No. EP07799466.3 dated Nov. 18, 2010, 9 pages.
European Search Report for Application No. EP08746822.9 dated Mar. 29, 2010, 7 Pages.
Examination Communication for Application No. EP06734083.6 dated May 18, 2010, 3 Pages.
Extended European Search Report for Application No. EP06734083.6 dated Jul. 1, 2009, 6 pages.
Fieguth H.G., et al., "Inhibition of Atrial Fibrillation by Pulmonary Vein Isolation and Auricular Resection—Experimental Study in a Sheep Model," The European Journal of Cardio-Thoracic Surgery, 1997, vol. 11, pp. 714-721.
Final Office Action dated Mar. 1, 2010 for U.S. Appl. No. 12/117,655, filed May 8, 2008.
Final Office Action dated Jun. 2, 2011 for U.S. Appl. No. 12/117,655, filed May 8, 2008.
Final Office Action dated May 12, 2011 for U.S. Appl. No. 11/775,771, filed Jul. 10, 2007.
Final Office Action dated Sep. 16, 2010 for U.S. Appl. No. 11/828,267, filed Jul. 25, 2007.
Hoey M.F., et al., "Intramural Ablation Using Radiofrequency Energy Via Screw-Tip Catheter and Saline Electrode," Pacing and Clinical Electrophysiology, 1995, vol. 18, Part II, 487.
Huang, "Increase in the Lesion Size and Decrease in the Impedance Rise with a Saline Infusion Electrode Catheter for Radiofrequency," Circulation, 1989, vol. 80 (4), II-324.
Moser K.M., et al., "Angioscopic Visualization of Pulmonary Emboli," Chest, 1980, vol. 77 (2), pp. 198-201.
Nakamura F., et al., "Percutaneous Intracardiac Surgery With Cardioscopic Guidance," SPIE, 1992, vol. 1642, pp. 214-216.
Non-Final Office Action dated Jun. 7, 2011 for U.S. Appl. No. 12/323,281, filed Nov. 25, 2008.
Non-Final Office Action dated Jun. 8, 2009 for U.S. Appl. No. 12/117,655, filed May 8, 2008.
Non-Final Office Action dated May 9, 2011 for U.S. Appl. No. 11/961,950, filed Dec. 20, 2007.
Non-Final Office Action dated May 9, 2011 for U.S. Appl. No. 11/961,995, filed Dec. 20, 2007.
Non-Final Office Action dated May 9, 2011 for U.S. Appl. No. 11/962,029, filed Dec. 20, 2007.
Non-Final Office Action dated Jun. 10, 2010 for U.S. Appl. No. 11/560,742, filed Nov. 16, 2006.
Non-Final Office Action dated Apr. 11, 2011 for U.S. Appl. No. 11/763,399, filed Jun. 14, 2007.
Non-Final Office Action dated Mar. 11, 2011 for U.S. Appl. No. 11/848,202, filed Aug. 30, 2007.
Non-Final Office Action dated May 11, 2011 for U.S. Appl. No. 11/828,267, filed Jul. 25, 2007.
Non-Final Office Action dated Apr. 12, 2011 for U.S. Appl. No. 12/499,011, filed Jul. 7, 2009.
Non-Final Office Action dated Jan. 14, 2010 for U.S. Appl. No. 11/828,267, filed Jul. 25, 2007.
Non-Final Office Action dated Dec. 16, 2010 for U.S. Appl. No. 12/117,655, filed May 8, 2008.
Non-Final Office Action dated Feb. 18, 2011 for U.S. Appl. No. 12/947,198, filed Nov. 16, 2010.
Non-Final Office Action dated Feb. 18, 2011 for U.S. Appl. No. 12/947,246, filed Nov. 16, 2006.
Non-Final Office Action dated May 20, 2011 for U.S. Appl. No. 11/775,819, filed Jul. 10, 2007.
Non-Final Office Action dated May 20, 2011 for U.S. Appl. No. 11/877,386, filed Oct. 23, 2007.
Non-Final Office Action dated Jul. 21, 2010 for U.S. Appl. No. 11/687,597, filed Mar. 16, 2007.
Non-Final Office Action dated May 23, 2011 for U.S. Appl. No. 11/775,837, filed Jul. 10, 2007.
Non-Final Office Action dated Nov. 24, 2010 for U.S. Appl. No. 11/848,429, filed Aug. 31, 2007.
Non-Final Office Action dated Nov. 24, 2010 for U.S. Appl. No. 12/464,800, filed May 12, 2009.
Non-Final Office Action dated Apr. 25, 2011 for U.S. Appl. No. 11/959,158, filed Dec. 18, 2007.
Non-Final Office Action dated Feb. 25, 2010 for U.S. Appl. No. 11/259,498, filed Oct. 25, 2005.
Non-Final Office Action dated Feb. 25, 2011 for U.S. Appl. No. 11/848,207, filed Aug. 30, 2007.
Non-Final Office Action dated Apr. 26, 2011 for U.S. Appl. No. 11/848,532, filed Aug. 31, 2007.
Non-Final Office Action dated Apr. 27, 2011 for U.S. Appl. No. 11/828,281, filed Jul. 25, 2007.
Non-Final Office Action dated Aug. 27, 2010 for U.S. Appl. No. 11/775,771, filed Jul. 10, 2007.
Non-Final Office Action dated Dec. 27, 2010 for U.S. Appl. No. 12/026,455, filed Feb. 5, 2008.
Notice of Allowance dated Feb. 3, 2011 for U.S. Appl. No. 11/560,732, filed Nov. 16, 2006.
Notice of Allowance dated Nov. 15, 2010 for U.S. Appl. No. 11/259,498, filed Oct. 25, 2005.
Notice of Allowance dated Nov. 15, 2010 for U.S. Appl. No. 11/560,742, filed Nov. 16, 2006.
Notice of Allowance dated Feb. 24, 2011 for U.S. Appl. No. 11/560,732, filed Mar. 16, 2007.
Notice of Allowance dated Feb. 24, 2011 for U.S. Appl. No. 11/687,597, filed Mar. 16, 2007.
Office Action dated Feb. 15, 2011 for Japanese Application No. 2007-554156 filed Jan. 30, 2006.
Office Action dated Apr. 27, 2011 for Japanese Application No. 2009-500630 filed Mar. 16, 2007.
Pappone C., et al., "Circumferential Radiofrequency Ablation of Pulmonary Vein Ostia," Circulation, 2000, vol. 102, pp. 2619-2628.

(56) References Cited

OTHER PUBLICATIONS

Sethi K.K., et al., "Transseptal catheterization for the electrophysiologist: modification with a 'view'," Journal of Interventional Cardiac Electrophysiology, 2001, vol. 5 (1), pp. 97-99.

Supplemental European Search Report for Application No. EP07758716 dated Feb. 28, 2011, 8 Pages.

Supplementary European search report for Application No. EP07812146.4 dated Nov. 18, 2010, 8 Pages.

Supplementary European Search Report for Application No. EP07841754, dated Jun. 30, 2010, 6 pages.

Thiagalingam A., et al., "Cooled Needle Catheter Ablation Creates Deeper and Wider Lesions than Irrigated Tip Catheter Ablation," Journal of Cardiovascular Electrophysiology, 2005, vol. 16 (5), pp. 1-8.

Uchida Y., "Developmental History of Cardioscopes", in: Coronary Angioscopy, Chapter 19, Futura Publishing Company, Inc., 2001, pp. 187-197.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Willkampf F.H., et al., "Radiofrequency Ablation with a Cooled Porous Electrode Catheter," JACC, Abstract, 1988, vol. 11 (2), pp. 17A.

\* cited by examiner

STENT DELIVERY UNDER DIRECT VISUALIZATION

CROSS-REFERENCE TO RELATED APPLICATIONS

This application is a continuation of U.S. patent application Ser. No. 16/359,447 filed Mar. 20, 2019, which is a division of U.S. patent application Ser. No. 14/490,107 filed Sep. 18, 2014 which is a continuation of U.S. patent application Ser. No. 12/367,019, filed Feb. 6, 2009, which claims the benefit of priority to U.S. Prov. Pat. App. 61/026,795 filed Feb. 7, 2008, all of which are incorporated herein by reference in their entirety.

FIELD OF THE INVENTION

The present invention relates generally to stent delivery systems which may be used to place one or more stents along a lesion. More particularly, the present invention relates to methods and apparatus for the delivery of one or more stents along a lesion, such as an ostial lesion or along a stenosed region (e.g., caused by atherosclerotic plaque) at various locations, for instance along the coronary vessels, renal arteries, etc., while directly visualizing the tissue region.

BACKGROUND OF THE INVENTION

Conventional devices for visualizing interior regions of a body lumen are known. For example, ultrasound devices have been used to produce images from within a body in vivo. Ultrasound has been used both with and without contrast agents, which typically enhance ultrasound-derived images.

Other conventional methods have utilized catheters or probes having position sensors deployed within the body lumen, such as the interior of a cardiac chamber. These types of positional sensors are typically used to determine the movement of a cardiac tissue surface or the electrical activity within the cardiac tissue. When a sufficient number of points have been sampled by the sensors, a "map" of the cardiac tissue may be generated.

Another conventional device utilizes an inflatable balloon which is typically introduced intravascularly in a deflated state and then inflated against the tissue region to be examined. Imaging is typically accomplished by an optical fiber or other apparatus such as electronic chips for viewing the tissue through the membrane(s) of the inflated balloon. Moreover, the balloon must generally be inflated for imaging. Other conventional balloons utilize a cavity or depression formed at a distal end of the inflated balloon. This cavity or depression is pressed against the tissue to be examined and is flushed with a clear fluid to provide a clear pathway through the blood.

However, such imaging balloons have many inherent disadvantages. For instance, such balloons generally require that the balloon be inflated to a relatively large size which may undesirably displace surrounding tissue and interfere with fine positioning of the imaging system against the tissue. Moreover, the working area created by such inflatable balloons are generally cramped and limited in size. Furthermore, inflated balloons may be susceptible to pressure changes in the surrounding fluid. For example, if the environment surrounding the inflated balloon undergoes pressure changes, e.g., during systolic and diastolic pressure cycles in a beating heart, the constant pressure change may affect the inflated balloon volume and its positioning to produce unsteady or undesirable conditions for optimal tissue imaging. Additionally, imaging balloons are subject to producing poor or blurred tissue images if the balloon is not firmly pressed against the tissue surface because of intervening blood between the balloon and tissue.

Accordingly, these types of imaging modalities are generally unable to provide desirable images useful for sufficient diagnosis and therapy of the endoluminal structure, due in part to factors such as dynamic forces generated by the natural movement of the heart. Moreover, anatomic structures within the body can occlude or obstruct the image acquisition process. Also, the presence and movement of opaque bodily fluids such as blood generally make in vivo imaging of tissue regions within the heart difficult.

Other external imaging modalities are also conventionally utilized. For example, computed tomography (CT) and magnetic resonance imaging (MRI) are typical modalities which are widely used to obtain images of body lumens such as the interior chambers of the heart. However, such imaging modalities fail to provide real-time imaging for intra-operative therapeutic procedures. Fluoroscopic imaging, for instance, is widely used to identify anatomic landmarks within the heart and other regions of the body. However, fluoroscopy fails to provide an accurate image of the tissue quality or surface and also fails to provide for instrumentation for performing tissue manipulation or other therapeutic procedures upon the visualized tissue regions. In addition, fluoroscopy provides a shadow of the intervening tissue onto a plate or sensor when it may be desirable to view the intraluminal surface of the tissue to diagnose pathologies or to perform some form of therapy on it.

In one particular treatment, intravascular stents are commonly used to maintain the patency of a vascular lumen. Conventional stent delivery systems typically employ intravascular ultrasound (IVUS) for selecting the appropriate stent and placing it at the site of lesions, e.g., ostial lesions. However, such assessment and placement methods are not accurate. For instance, the treatment site may be located in the right coronary artery immediately adjacent to the ostium in the aortic wall. In such instances, it is often difficult to accurately position an intravascular stem such that the stent does not extend too far proximal to the ostium. Accuracy in placing the stent at the desired location is typically affected by, e.g., limited visualization of the ostium, angulations of the aorto-coronary segment, and the difficulties in the placement of the guiding catheter.

Accurate positioning of the stent along the ostial lesion is particularly desirable because (a) if the stent is placed too proximal to the ostium, the protrusion of the stent into the aortic lumen can cause thrombus or other complications; and (b) if the stent is placed too distal to the ostium, the stent may not be able to subdue the ostial lesion completely thereby resulting in low success rate and high incidence of re-stenosis or recurrence of arterial blockage.

Thus, methods and/or apparatus which are able to allow for accurate positioning of the stent relative to the ostial lesion is highly desirable.

SUMMARY OF THE INVENTION

A tissue imaging and manipulation apparatus that may be utilized for procedures within a body lumen, such as the heart, in which visualization of the surrounding tissue is made difficult, if not impossible, by medium contained within the lumen such as blood, is described below. Generally, such a tissue imaging and manipulation apparatus comprises an optional delivery catheter or sheath through which a deployment catheter and imaging hood may be advanced for placement against or adjacent to the tissue to be imaged.

The deployment catheter may define a fluid delivery lumen therethrough as well as an imaging lumen within which an optical imaging fiber or assembly may be disposed for imaging tissue. When deployed, the imaging hood may be expanded into any number of shapes, e.g., cylindrical, conical as shown, semi-spherical, etc., provided that an open area or field is defined by the imaging hood. The open area is the area within which the tissue region of interest may be imaged. The imaging hood may also define an atraumatic contact lip or edge for placement or abutment against the tissue region of interest. Moreover, the distal end of the deployment catheter or separate manipulatable catheters may be articulated through various controlling mechanisms such as push-pull wires manually or via computer control The deployment catheter may also be stabilized relative to the tissue surface through various methods. For instance, inflatable stabilizing balloons positioned along a length of the catheter may be utilized, or tissue engagement anchors may be passed through or along the deployment catheter for temporary engagement of the underlying tissue.

In operation, after the imaging hood has been deployed, fluid may be pumped at a positive pressure through the fluid delivery lumen until the fluid fills the open area completely and displaces any blood from within the open area. The fluid may comprise any biocompatible fluid, e.g., saline, water, plasma, Fluorinert™, etc., which is sufficiently transparent to allow for relatively undistorted visualization through the fluid. The fluid may be pumped continuously or intermittently to allow for image capture by an optional processor which may be in communication with the assembly.

In an exemplary variation for imaging tissue surfaces within a heart chamber containing blood, the tissue imaging and treatment system may generally comprise a catheter body having a lumen defined therethrough, a visualization element disposed adjacent the catheter body, the visualization element having a field of view, a transparent fluid source in fluid communication with the lumen, and a barrier or membrane extendable from the catheter body to localize, between the visualization element and the field of view, displacement of blood by transparent fluid that flows from the lumen, and an instrument translatable through the displaced blood for performing any number of treatments upon the tissue surface within the field of view. The imaging hood may be formed into any number of configurations and the imaging assembly may also be utilized with any number of therapeutic tools which may be deployed through the deployment catheter.

More particularly in certain variations, the tissue visualization system may comprise components including the imaging hood, where the hood may further include a membrane having a main aperture and additional optional openings disposed over the distal end of the hood. An introducer sheath or the deployment catheter upon which the imaging hood is disposed may further comprise a steerable segment made of multiple adjacent links which are pivotably connected to one another and which may be articulated within a single plane or multiple planes. The deployment catheter itself may be comprised of a multiple lumen extrusion, such as a four-lumen catheter extrusion, which is reinforced with braided stainless steel fibers to provide structural support. The proximal end of the catheter may be coupled to a handle for manipulation and articulation of the system.

To provide visualization, an imaging element such as a fiberscope or electronic imager such as a solid state camera, e.g., CCD or CMOS, may be mounted, e.g., on a shape memory wire, and positioned within or along the hood interior. A fluid reservoir and/or pump (e.g., syringe, pressurized intravenous bag, etc.) may be fluidly coupled to the proximal end of the catheter to hold the translucent fluid such as saline or contrast medium as well as for providing the pressure to inject the fluid into the imaging hood.

In treating tissue regions which are directly visualized, as described above, one particular treatment involves deploying a stent within a vessel lumen or ostium while under direct visualization. An introducer sheath may be introduced into the patient's body utilizing conventional approaches such that the sheath is advanced intravascularly through the aorta where a guidewire may be advanced through the sheath and into, e.g., the right coronary artery. The treatment may be affected not only within and around the right coronary artery, but also the left coronary artery, left anterior descending artery, left circumflex artery, or any other vessel accessible by the assembly. As the guidewire is positioned within, e.g., the vessel lumen, the deployment catheter and hood may be deployed from the sheath and advanced along the guidewire until the circumference of the hood contacts against or in proximity to the ostium. Once the hood is in contact against the ostium, the clearing fluid may be introduced within the open area of the hood to purge the blood from the hood interior to provide a clear field through which an imaging element positioned within or along the hood may visualize through to view the underlying tissue surrounding the ostium and at least a portion of the vessel wall extending into the lumen.

A stent delivery assembly having an inflatable balloon in an un-inflated low-profile configuration and a stent crimped or otherwise positioned upon the balloon may be advanced through the catheter and distally out from the hood until the stent assembly is positioned in proximity or adjacent to, e.g., an ostial lesion, which is to be treated. The imaging element may be used to directly visualize at least partially into the lumen as the purged clearing fluid exits the hood and down through the lumen to provide an image of the lesion to be treated.

With the stent assembly desirably positioned and confirmed by direct visualization, the balloon may be inflated to expand the stent over the lesion, also while under visualization. In other variations, the balloon carrying the stent may be integrated with a visualization balloon positioned proximally of the stent assembly rather than a hood. The balloon may be subsequently deflated and then retracted back into the hood and the catheter leaving the deployed stent positioned desirably within the lumen. The imager may be used to visually confirm the deployment and positioning of the stent within the lumen.

In determining the size of the ostial lesion to be treated, the imaging capabilities of the hood may be utilized for optimally treating the patient by directly measuring not only the lesion but also the diameter of the vessel lumen for determining an appropriate stent to be deployed as the diameter of the vessel as well as the axial length of the lesion may affect the shape and size of the stent.

One example utilizes a measurement catheter having a number of gradations with known distances which may be advanced through the hood and into the lumen. With the purging fluid introduced through the hood and into the lumen, the markings on the catheter may be viewed and compared to the lesion directly to provide a more accurate measurement of the lesion length than provided by a fluoroscopic image alone. In other variations, expandable baskets or members each having a known expanded diameter may be positioned along a support catheter and advanced distally from the hood and into the lumen to measure a diameter of the vessel interior. The inner diameter of the vessel can thus be calculated by considering the diameter of the member which is blocked from entering the ostium. With the calculated length and diameter of the vessel and lesion to be treated, an appropriate stent may be selected for placement at the ostial lesion.

In yet another variation, a deployment catheter may utilize a hood having an angled interface which is angled relative to the catheter. The asymmetric slanted hood may be used to facilitate navigation within the aorta as the hood may be better able to engage against a tissue region or ostium and establish visualization without the need to steer and/or articulate the catheter shaft perpendicularly within the narrow aorta lumen.

DETAILED DESCRIPTION OF THE INVENTION

A tissue-imaging and manipulation apparatus described herein is able to provide real-time images in vivo of tissue regions within a body lumen such as a heart, which is filled with blood flowing dynamically therethrough and is also able to provide intravascular tools and instruments for performing various procedures upon the imaged tissue regions. Such an apparatus may be utilized for many procedures, e.g., facilitating transseptal access to the left atrium, cannulating the coronary sinus, diagnosis of valve regurgitation/stenosis, valvuloplasty, atrial appendage closure, arrhythmogenic focus ablation, among other procedures.

Figure 1A:
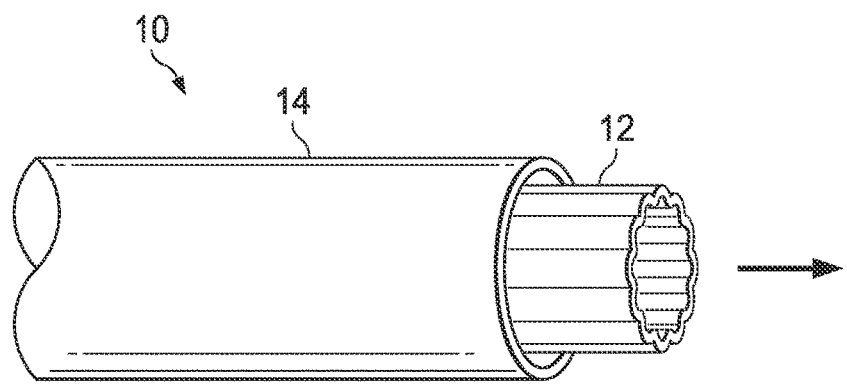
FIG. 1A shows a side view of one variation of a tissue imaging apparatus during deployment from a sheath or delivery catheter.
Figure 1B:
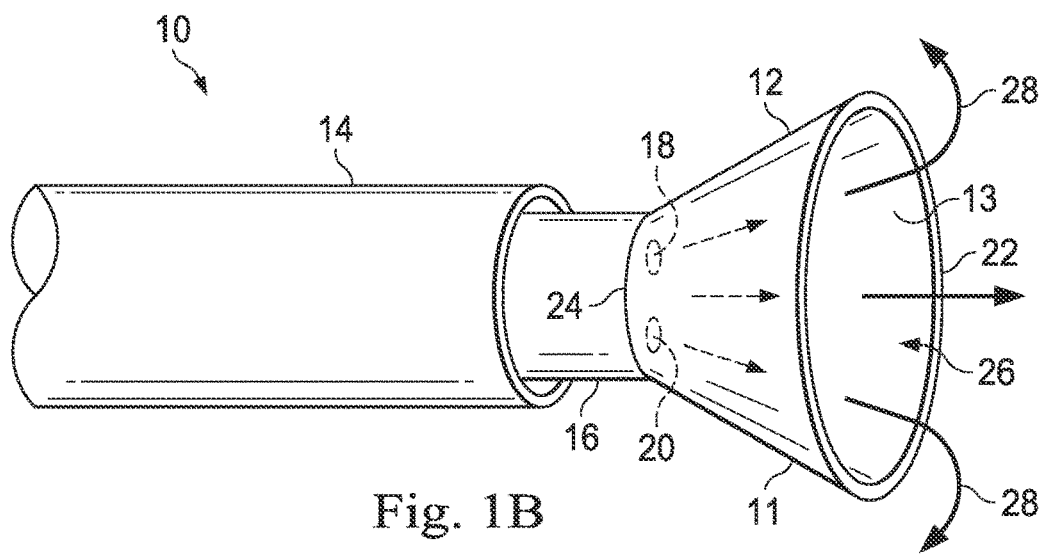
FIG. 1B shows the deployed tissue imaging apparatus of FIG. 1A having an optionally expandable hood or sheath attached to an imaging and/or diagnostic catheter.
Figure 1C:
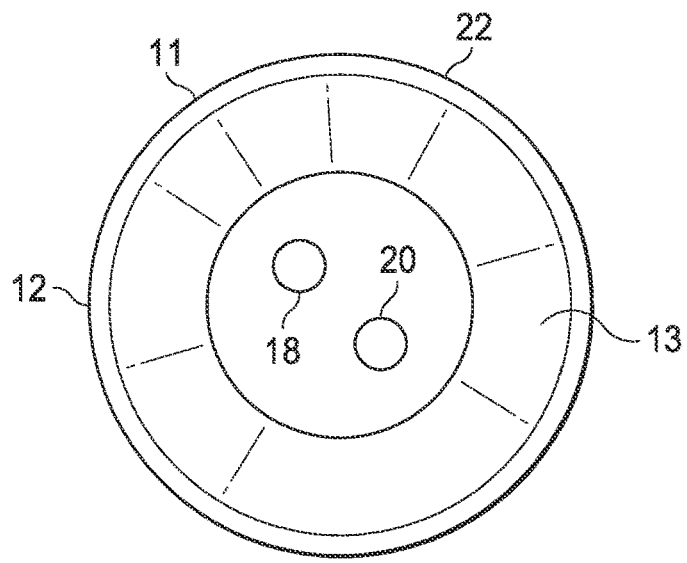
FIG. 1C shows an end view of a deployed imaging apparatus.

One variation of a tissue access and imaging apparatus is shown in the detail perspective views of FIGS. 1A to 1C. As shown in FIG. 1A, tissue imaging and manipulation assembly 10 may be delivered intravascularly through the patient's body in a low-profile configuration via a delivery catheter or sheath 14. In the case of treating tissue, it is generally desirable to enter or access the left atrium while minimizing trauma to the patient. To non-operatively effect such access, one conventional approach involves puncturing the intra-atrial septum from the right atrial chamber to the left atrial chamber in a procedure commonly called a transseptal procedure or septostomy. For procedures such as percutaneous valve repair and replacement, transseptal access to the left atrial chamber of the heart may allow for larger devices to be introduced into the venous system than can generally be introduced percutaneously into the arterial system.

When the imaging and manipulation assembly 10 is ready to be utilized for imaging tissue, imaging hood 12 may be advanced relative to catheter 14 and deployed from a distal opening of catheter 14, as shown by the arrow. Upon deployment, imaging hood 12 may be unconstrained to expand or open into a deployed imaging configuration, as shown in FIG. 1B. Imaging hood 12 may be fabricated from a variety of pliable or conformable biocompatible material including but not limited to, e.g., polymeric, plastic, or woven materials. One example of a woven material is Kevlar® (E. I. du Pont de Nemours, Wilmington, DE), which is an aramid and which can be made into thin, e.g., less than 0.001 in., materials which maintain enough integrity for such applications described herein. Moreover, the imaging hood 12 may be fabricated from a translucent or opaque material and in a variety of different colors to optimize or attenuate any reflected lighting from surrounding fluids or structures, i.e., anatomical or mechanical structures or instruments. In either case, imaging hood 12 may be fabricated into a uniform structure or a scaffold-supported structure, in which case a scaffold made of a shape memory alloy, such as Nitinol, or a spring steel, or plastic, etc., may be fabricated and covered with the polymeric, plastic, or woven material. Hence, imaging hood 12 may comprise any of a wide variety of barriers or membrane structures, as may generally be used to localize displacement of blood or the like from a selected volume of a body lumen or heart chamber. In exemplary embodiments, a volume within an inner surface 13 of imaging hood 12 will be significantly less than a volume of the hood 12 between inner surface 13 and outer surface 11.

Imaging hood 12 may be attached at interface 24 to a deployment catheter 16 which may be translated independently of deployment catheter or sheath 14. Attachment of interface 24 may be accomplished through any number of conventional methods. Deployment catheter 16 may define a fluid delivery lumen 18 as well as an imaging lumen 20 within which an optical imaging fiber or assembly may be disposed for imaging tissue. When deployed, imaging hood 12 may expand into any number of shapes, e.g., cylindrical, conical as shown, semi-spherical, etc., provided that an open area or field 26 is defined by imaging hood 12. The open area 26 is the area within which the tissue region of interest may be imaged. Imaging hood 12 may also define an atraumatic contact lip or edge 22 for placement or abutment against the tissue region of interest. Moreover, the diameter of imaging hood 12 at its maximum fully deployed diameter, e.g., at contact lip or edge 22, is typically greater relative to a diameter of the deployment catheter 16 (although a diameter of contact lip or edge 22 may be made to have a smaller or equal diameter of deployment catheter 16). For instance, the contact edge diameter may range anywhere from 1 to 5 times (or even greater, as practicable) a diameter of deployment catheter 16. FIG. 1C shows an end view of the imaging hood 12 in its deployed configuration. Also shown are the contact lip or edge 22 and fluid delivery lumen 18 and imaging lumen 20.

Figure 2A:
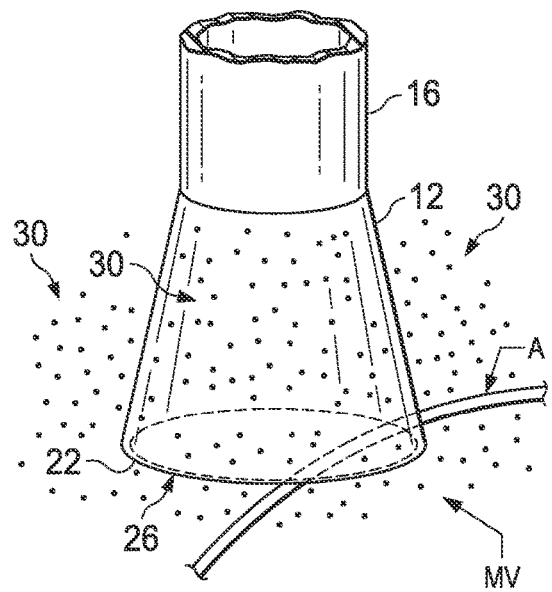
FIGS. 2A and 2B show one example of a deployed tissue imager positioned against or adjacent to the tissue to be imaged and a flow of fluid, such as saline, displacing blood from within the expandable hood.
Figure 2B:
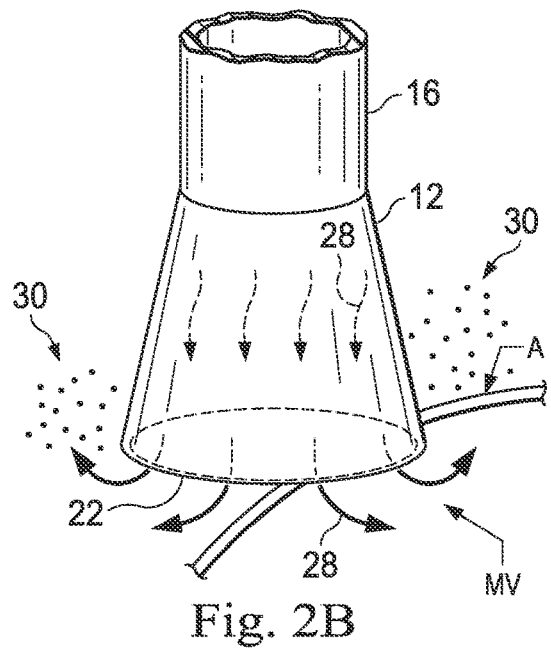

As seen in the example of FIGS. 2A and 2B, deployment catheter 16 may be manipulated to position deployed imaging hood 12 against or near the underlying tissue region of interest to be imaged, in this example a portion of annulus A of mitral valve MV within the left atrial chamber. As the surrounding blood 30 flows around imaging hood 12 and within open area 26 defined within imaging hood 12, as seen in FIG. 2A, the underlying annulus A is obstructed by the opaque blood 30 and is difficult to view through the imaging lumen 20. The translucent fluid 28, such as saline, may then be pumped through fluid delivery lumen 18, intermittently or continuously, until the blood 30 is at least partially, and preferably completely, displaced from within open area 26 by fluid 28, as shown in FIG. 2B.

Although contact edge 22 need not directly contact the underlying tissue, it is at least preferably brought into close proximity to the tissue such that the flow of clear fluid 28 from open area 26 may be maintained to inhibit significant backflow of blood 30 back into open area 26. Contact edge 22 may also be made of a soft elastomeric material such as certain soft grades of silicone or polyurethane, as typically known, to help contact edge 22 conform to an uneven or rough underlying anatomical tissue surface. Once the blood 30 has been displaced from imaging hood 12, an image may then be viewed of the underlying tissue through the clear fluid 30. This image may then be recorded or available for real-time viewing for performing a therapeutic procedure. The positive flow of fluid 28 may be maintained continuously to provide for clear viewing of the underlying tissue. Alternatively, the fluid 28 may be pumped temporarily or sporadically only until a clear view of the tissue is available to be imaged and recorded, at which point the fluid flow 28 may cease and blood 30 may be allowed to seep or flow back into imaging hood 12. This process may be repeated a number of times at the same tissue region or at multiple tissue regions.

Figure 3A:
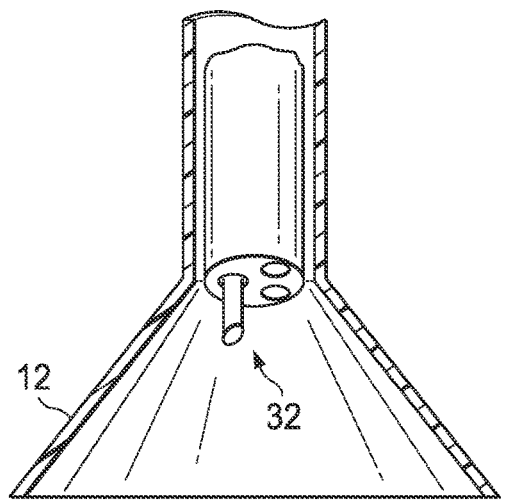
FIGS. 3A and 3B show examples of various visualization imagers which may be utilized within or along the imaging hood.
Figure 3B:
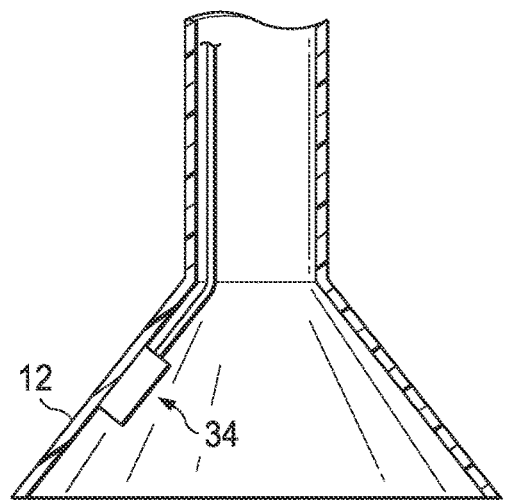

FIG. 3A shows a partial cross-sectional view of an example where one or more optical fiber bundles 32 may be positioned within the catheter and within imaging hood 12 to provide direct in-line imaging of the open area within hood 12. FIG. 3B shows another example where an imaging element 34 (e.g., CCD or CMOS electronic imager) may be placed along an interior surface of imaging hood 12 to provide imaging of the open area such that the imaging element 34 is off-axis relative to a longitudinal axis of the hood 12, as described in further detail below. The off-axis position of element 34 may provide for direct visualization and uninhibited access by instruments from the catheter to the underlying tissue during treatment.

Figure 4A:
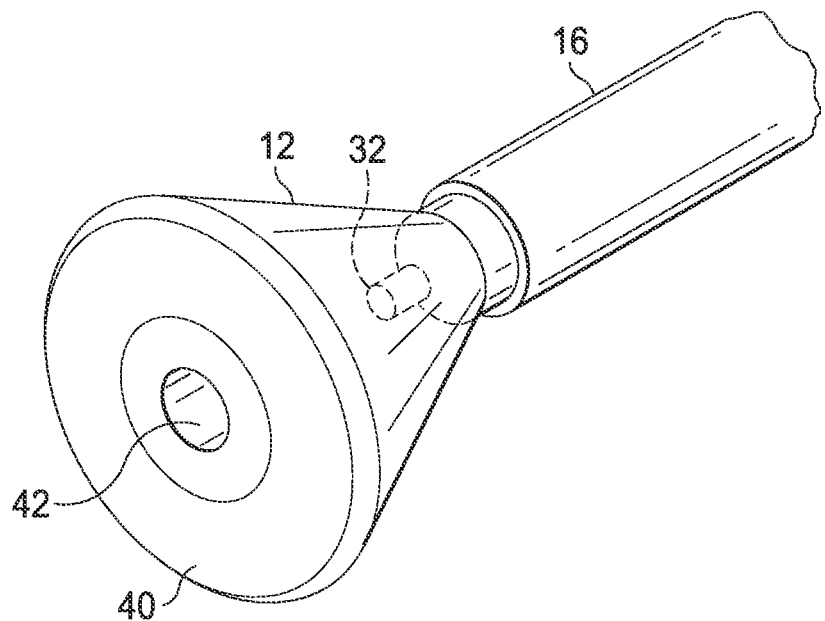
FIGS. 4A and 4B show perspective and end views, respectively, of an imaging hood having at least one layer of a transparent elastomeric membrane over the distal opening of the hood.
Figure 4B:
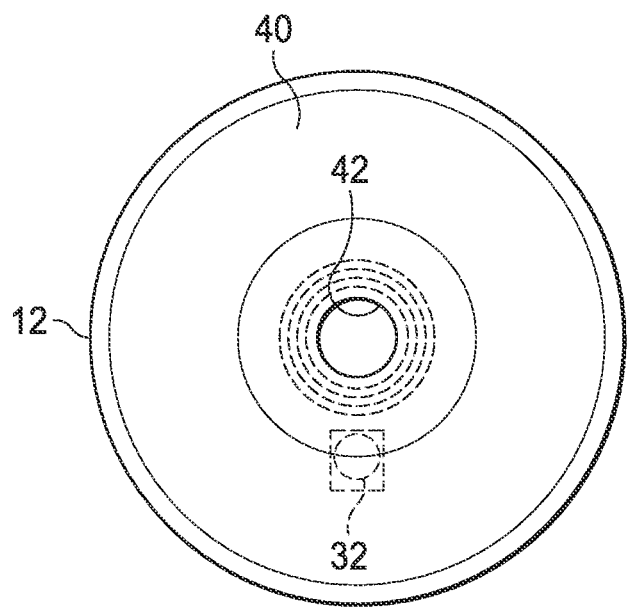

In utilizing the imaging hood 12 in any one of the procedures described herein, the hood 12 may have an open field which is uncovered and clear to provide direct tissue contact between the hood interior and the underlying tissue to effect any number of treatments upon the tissue, as described above. Yet in additional variations, imaging hood 12 may utilize other configurations. An additional variation of the imaging hood 12 is shown in the perspective and end views, respectively, of FIGS. 4A and 4B, where imaging hood 12 includes at least one layer of a transparent elastomeric membrane 40 over the distal opening of hood 12. An aperture 42 having a diameter which is less than a diameter of the outer lip of imaging hood 12 may be defined over the center of membrane 40 where a longitudinal axis of the hood intersects the membrane such that the interior of hood 12 remains open and in fluid communication with the environment external to hood 12. Furthermore, aperture 42 may be sized, e.g., between 1 to 2 mm or more in diameter and membrane 40 can be made from any number of transparent elastomers such as silicone, polyurethane, latex, etc. such that contacted tissue may also be visualized through membrane 40 as well as through aperture 42.

Aperture 42 may function generally as a restricting passageway to reduce the rate of fluid out-flow from the hood 12 when the interior of the hood 12 is infused with the clear fluid through which underlying tissue regions may be visualized. Aside from restricting out-flow of clear fluid from within hood 12, aperture 42 may also restrict external surrounding fluids from entering hood 12 too rapidly. The reduction in the rate of fluid out-flow from the hood and blood in-flow into the hood may improve visualization conditions as hood 12 may be more readily filled with transparent fluid rather than being filled by opaque blood which may obstruct direct visualization by the visualization instruments.

Moreover, aperture 42 may be aligned with catheter 16 such that any instruments (e.g., piercing instruments, guidewires, tissue engagers, etc.) that are advanced into the hood interior may directly access the underlying tissue uninhibited or unrestricted for treatment through aperture 42. In other variations wherein aperture 42 may not be aligned with catheter 16, instruments passed through catheter 16 may still access the underlying tissue by simply piercing through membrane 40.

Figure 5A:
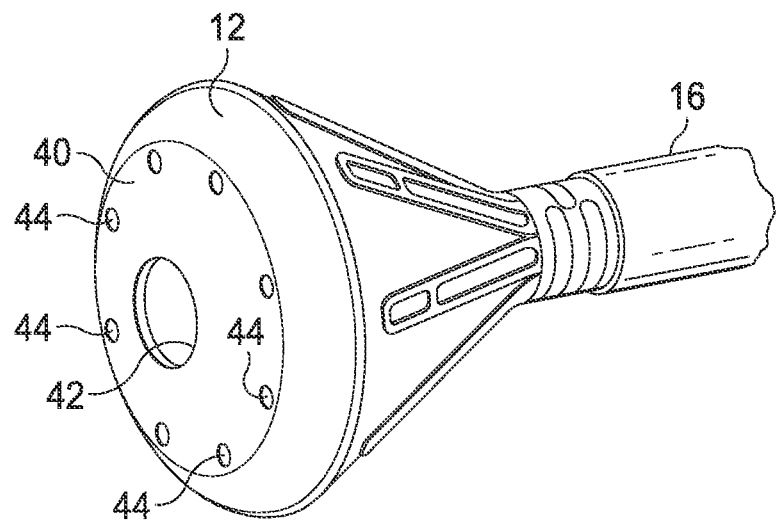
FIGS. 5A and 5B show perspective and end views, respectively, of an imaging hood which includes a membrane with an aperture defined therethrough and a plurality of additional openings defined over the membrane surrounding the aperture.
Figure 5B:
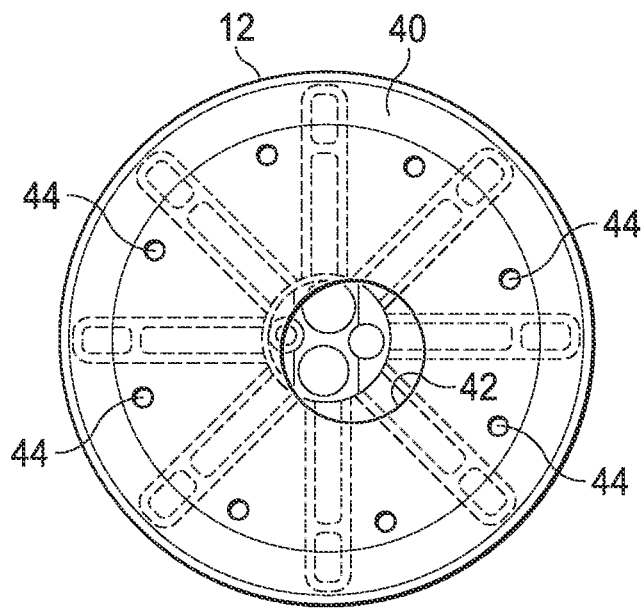

In an additional variation, FIGS. 5A and 5B show perspective and end views, respectively, of imaging hood 12 which includes membrane 40 with aperture 42 defined therethrough, as described above. This variation includes a plurality of additional openings 44 defined over membrane 40 surrounding aperture 42. Additional openings 44 may be uniformly sized, e.g., each less than 1 mm in diameter, to allow for the out-flow of the translucent fluid therethrough when in contact against the tissue surface. Moreover, although openings 44 are illustrated as uniform in size, the openings may be varied in size and their placement may also be non-uniform or random over membrane 40 rather than uniformly positioned about aperture 42 in FIG. 5B. Furthermore, there are eight openings 44 shown in the figures although fewer than eight or more than eight openings 44 may also be utilized over membrane 40.

Additional details of tissue imaging and manipulation systems and methods which may be utilized with apparatus and methods described herein are further described, for example, in U.S. patent application Ser. No. 11/259,498 filed Oct. 25, 2005 (U.S. Pat. Pub. No. 2006/0184048 A1, which is incorporated herein by reference in its entirety.

Figure 6:
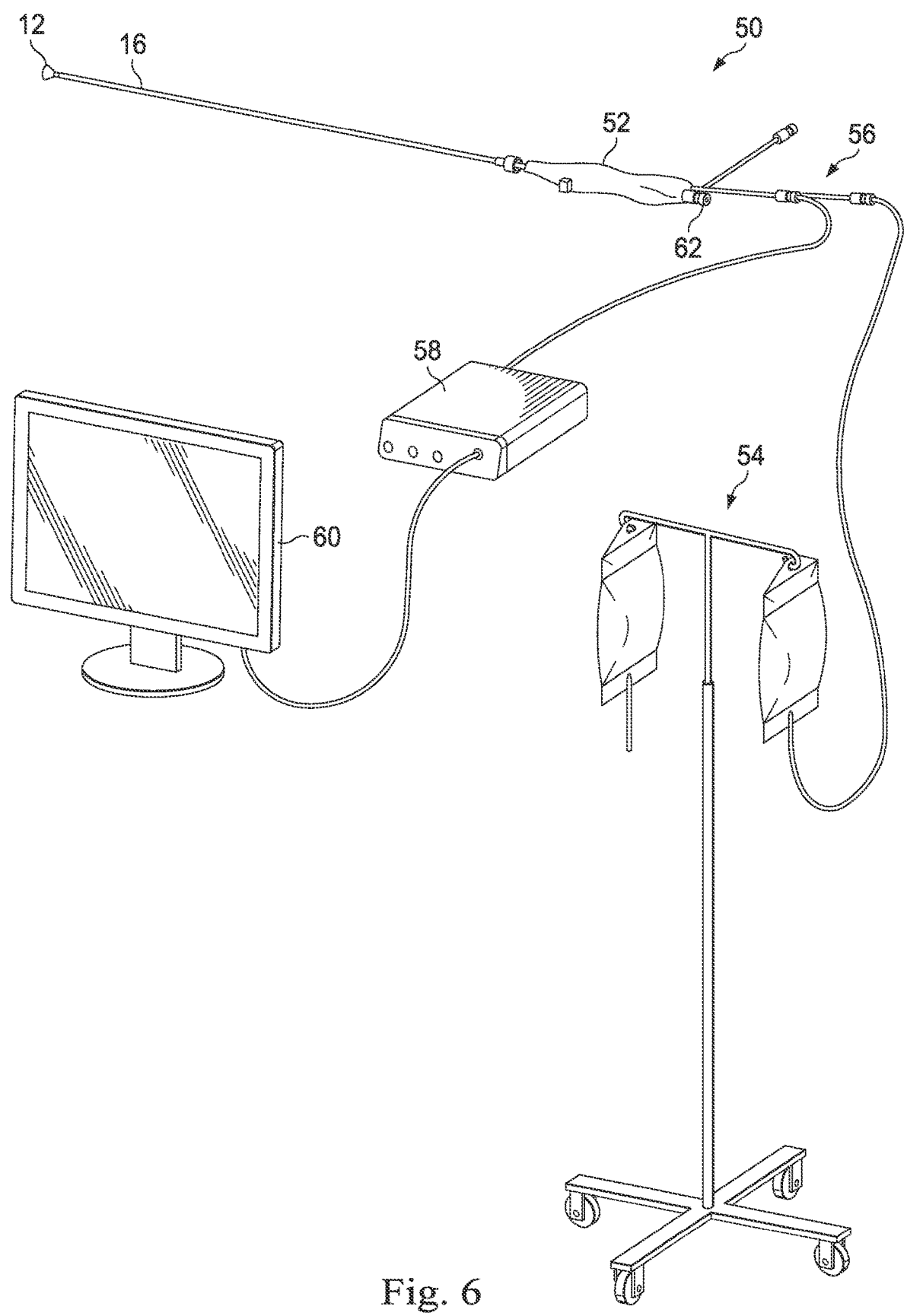
FIG. 6 illustrates an example of a system configured for visualization and stent delivery.

As the assembly allows for ablation of tissue directly visualized through hood 12, FIG. 6 illustrates an example of a system configured for visualization and stent delivery. As shown in visualization assembly 50, hood 12 and deployment catheter 16 are coupled to handle 52. Fluid reservoir 54, shown in this example as a saline-filled bag reservoir, may be attached through handle 52 to provide the clearing fluid and/or ablation medium. An optical imaging assembly 56 coupled to an imaging element 34 positioned within or adjacent to hood 12 may extend proximally through handle 52 and be coupled to imaging processor assembly 58 for processing the images detected within hood 12. The video processor assembly 58 may process the detected images within hood 12 for display upon video display 60. Handle 52 may further incorporate a delivery channel or port 62 through which a stent delivery assembly may be introduced for deployment of one or more stents into the patient's body through the deployment catheter 16 and hood 12.

Figure 7A:
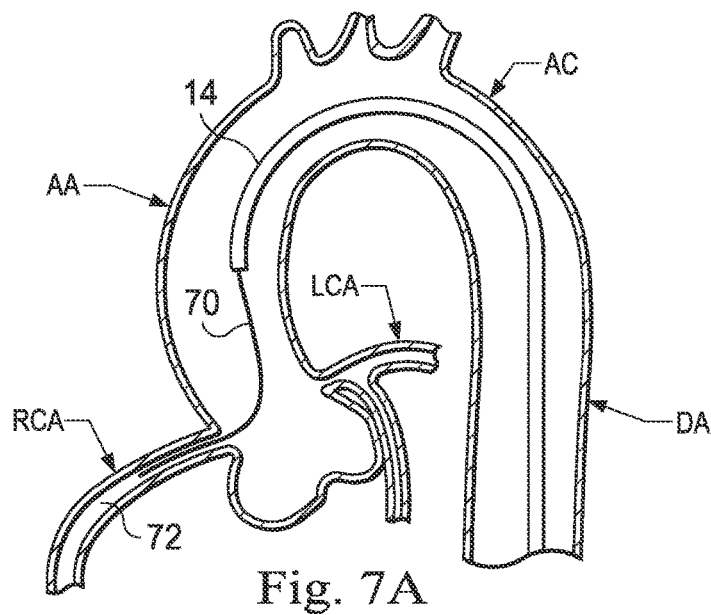
FIGS. 7A to 7C show partial cross-sectional views of deploying a stent intravascularly within a coronary artery while under direct visualization.
Figure 7B:
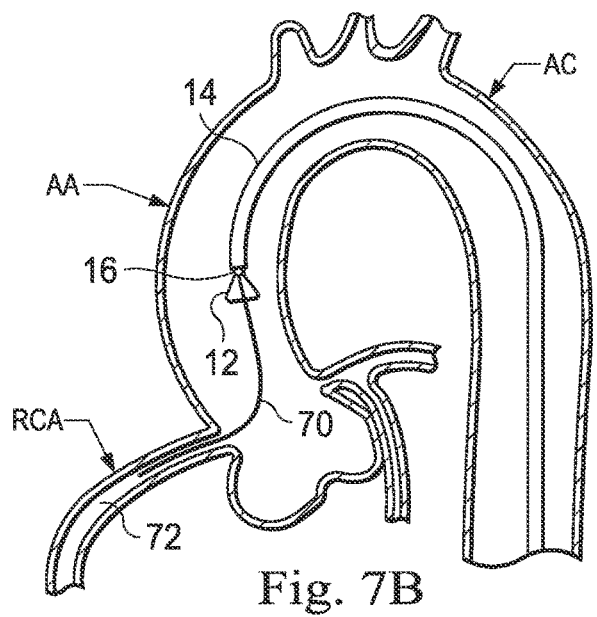
Figure 7C:
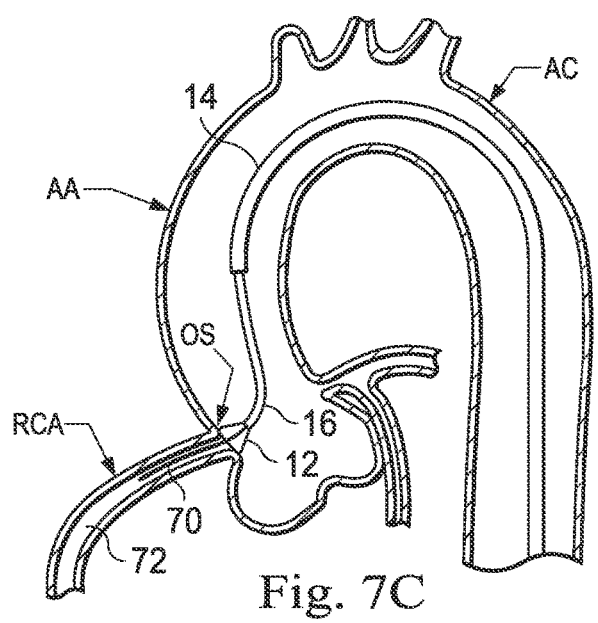

One example for deploying a stent while under direct visualization is shown in the partial cross-sectional views of FIGS. 7A to 7C. Introducer sheath 14 may be introduced into the patient's body utilizing conventional approaches such that the sheath 14 is advanced intravascularly through the descending aorta DA and aortic arch AC and into the ascending aorta AA, where a guidewire 70 may be advanced through sheath 14 and into, e.g., the right coronary artery RCA. Treatment may be affected not only within and around the right coronary artery RCA, but also the left coronary artery LCA, left anterior descending artery, left circumflex artery, or any other vessel accessible by the assembly. As the guidewire 70 is positioned within, e.g., the lumen 72 of RCA as shown in FIG. 7A, deployment catheter 16 and hood 12 may be deployed from sheath 14 and advanced along guidewire 70, as shown in FIG. 7B, until the circumference of hood 12 contacts against or in proximity to ostium OS. Guidewire 70 may be omitted from the procedure, if so desired.

Once hood 12 is in contact against the ostium OS, the clearing fluid may be introduced within the open area of hood 12 to purge the blood from the hood interior to provide a clear field through which an imaging element positioned within or along hood 12 may visualize through to view the underlying tissue surrounding the ostium OS and at least a portion of the vessel wall extending into lumen 72.

Figure 8A:
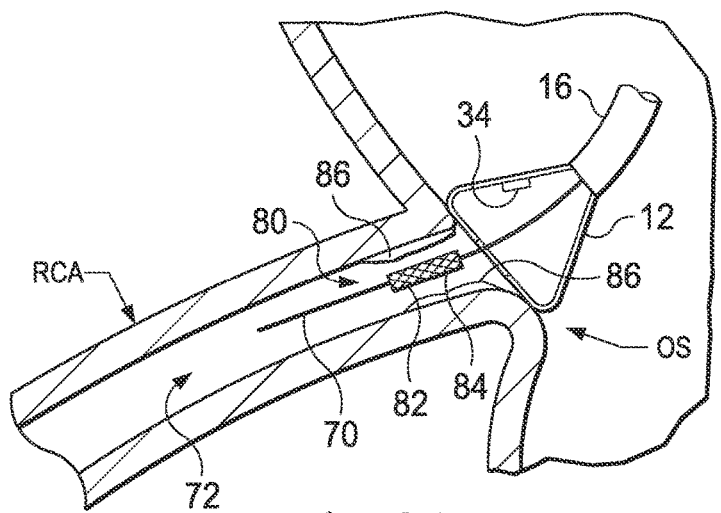
FIGS. 8A to 8C show partial cross-sectional detail views of a stent assembly introduced and deployed within a vessel while under direct visualization.
Figure 8B:
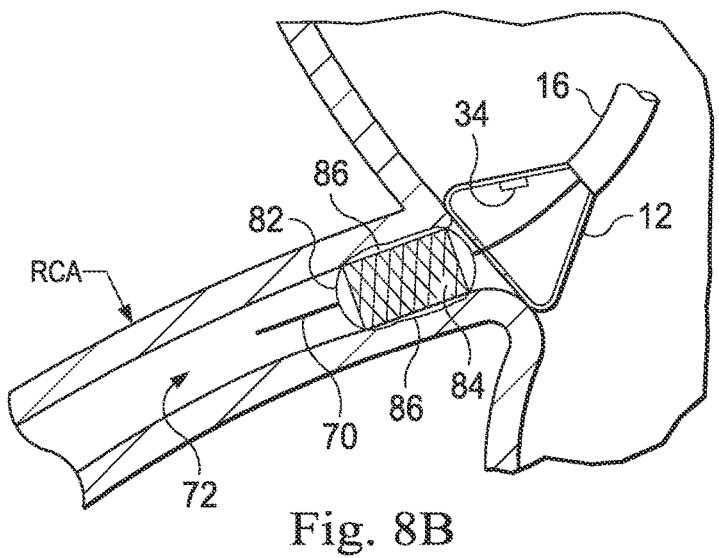
Figure 8C:
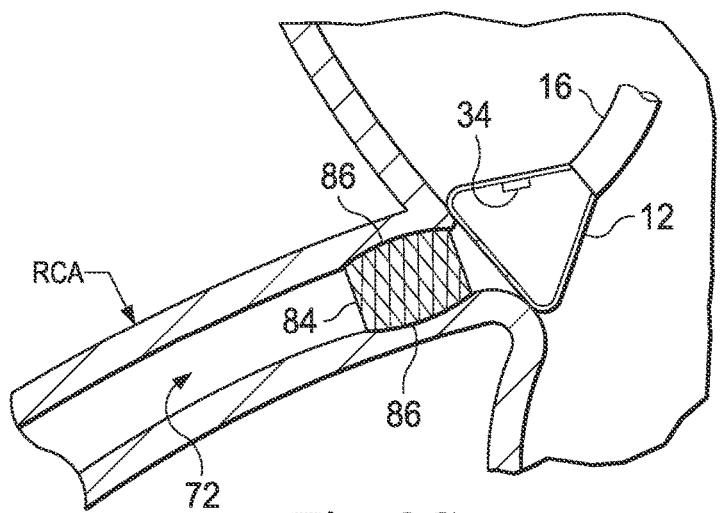

As illustrated in the detail partial cross-sectional views of FIGS. 8A to 8C, with hood 12 positioned against or in proximity to ostium OS and the visual field cleared to provide visual imaging by imager 34, a stent delivery assembly 80 having an inflatable balloon 82 in an un-inflated low-profile configuration and a stent 84 crimped or otherwise positioned upon balloon 82 may be advanced through catheter 16 and distally out from hood 12 until stent assembly 80 is positioned in proximity or adjacent to, e.g., an ostial lesion 86, which is to be treated, as shown in FIG. 8A. Imager 34 may be used to directly visualize at least partially into lumen 72 as the purged clearing fluid exits hood 12 and down through lumen 72 to provide an image of the lesion 86 to be treated.

With stent assembly 80 desirably positioned and confirmed by direct visualization, balloon 82 may be inflated to expand stent 84 over lesion 86, as shown in FIG. 8B, also while under visualization. Balloon 82 may be subsequently deflated and then retracted back into hood 12 and catheter 16 leaving the deployed stent 84 positioned desirably within lumen 72. Imager 34 may be used to visually confirm the deployment and positioning of stent 84 within lumen 72, as shown in FIG. 8C.

In determining the size of the ostial lesion to be treated, the imaging capabilities of the hood 12 may be utilized for optimally treating the patient by directly measuring not only the lesion but also the diameter of the vessel lumen for determining an appropriate stent to be deployed as the diameter of the vessel as well as the axial length of the lesion may affect the shape and size of the stent.

Figure 9A:
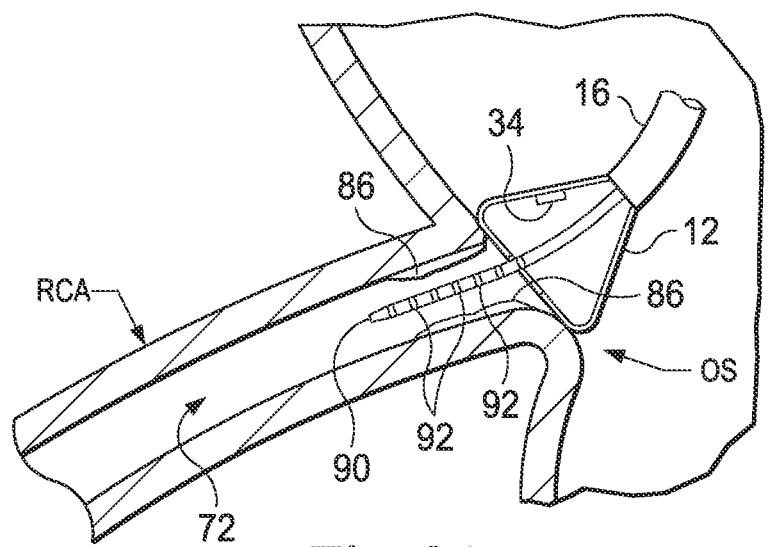
FIG. 9A shows a partial cross-sectional view of a measurement catheter deployed within a vessel for directly measuring a length of a lesion.

One example is illustrated in the partial cross-sectional area of FIG. 9A, which shows hood 12 positioned against ostium OS with imager 34 visualizing the encompassed tissue and lesion 86. A measurement catheter 90 having a number of gradations 92 with known distances may be advanced through hood 12 and into lumen 72. With the purging fluid introduced through hood 12 and into lumen 72, the markings on catheter 90 may be viewed and compared to the lesion 86 directly to provide a more accurate measurement of the lesion length than provided by a fluoroscopic image alone.

Figure 9B:
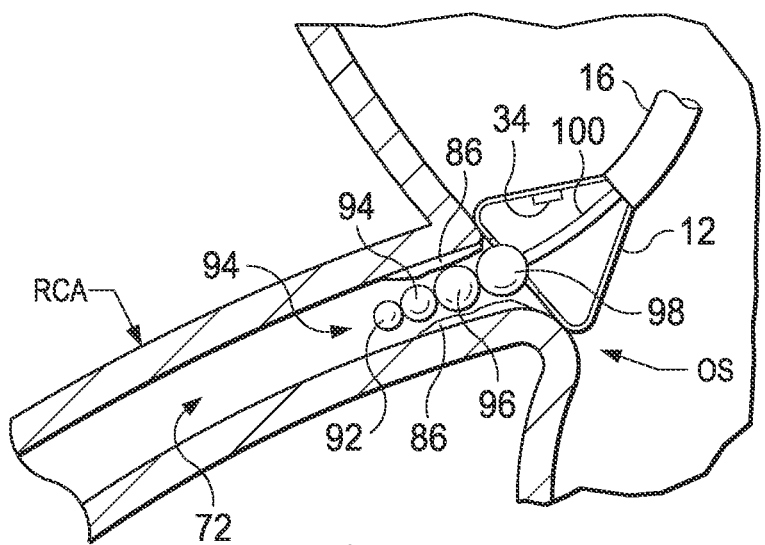
FIG. 9B shows a partial cross-sectional view of one or more measurement baskets or expandable members which may be utilized to measure an inner diameter of the vessel.

FIG. 9B shows another example where one or more measurement baskets or expandable members 92, 94, 96, 98 (e.g., wire or mesh baskets, distensible membranes, etc.) may be utilized to measure an inner diameter of the vessel. Expandable baskets or members each having a known expanded diameter may be positioned along a support catheter 100 and advanced distally from hood 12 and into lumen 72 to measure a diameter of the vessel interior. The one or more members may be positioned along catheter 100 in increasing order of diameter size with colors, designs, markings, or other visual indications used to identify each particular member. Although four members 92, 94, 96, 98 are shown in the example, as few as one member or greater than four members may be utilized. Moreover, each subsequent member may be stepped in diameter size by a predetermined amount as desired. The members may be passed through the vessel ostium while under visualization in increasing order of diameter until the expanded basket is compressed or unable to cannulate the ostium OS. The inner diameter of the vessel can thus be calculated by considering the diameter of the member which is blocked from entering ostium OS. With the calculated length and diameter of the vessel and lesion to be treated, an appropriate stent 84 may be selected for placement at the ostial lesion 86.

Figure 10A:
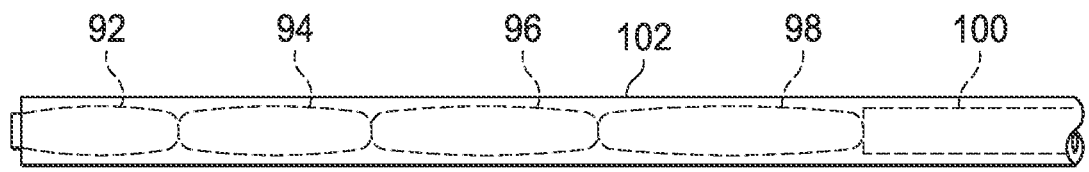
FIGS. 10A to 10C illustrate side views of measurement baskets or expandable members which may be deployed sequentially in determining the inner diameter of a vessel.
Figure 10B:
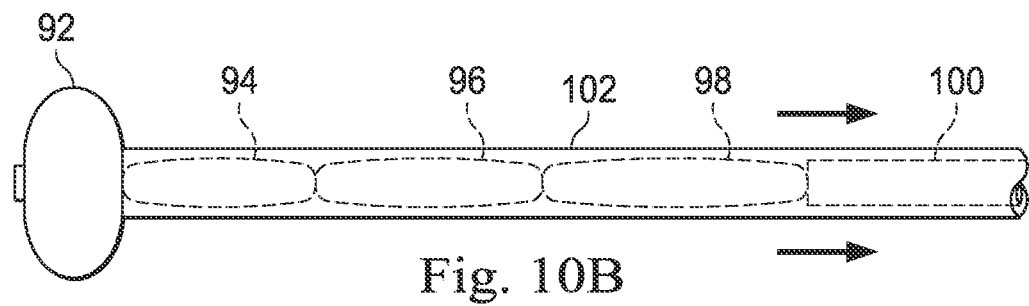
Figure 10C:
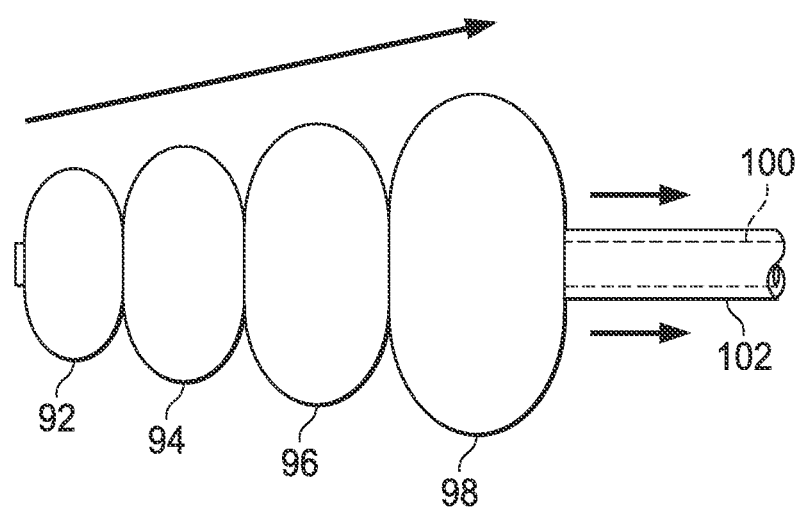

In use, catheter 100 may be advanced through hood 12 with the one or more measurement baskets or expandable members 92, 94, 96, 98 configured in a delivery profile while constrained within sheath 102, as shown in the detail side view of FIG. 10A. Sheath 102 may be retracted, as indicated by the arrows, or catheter 100 may be advanced distally until each respective member is deployed and expanded, as shown in FIG. 10B, until all the members 92, 94, 96, 98 or an appropriate number of members have been deployed and expanded within the vessel lumen and/or proximate to the ostium OS, as shown in FIG. 10C.

Figure 11A:
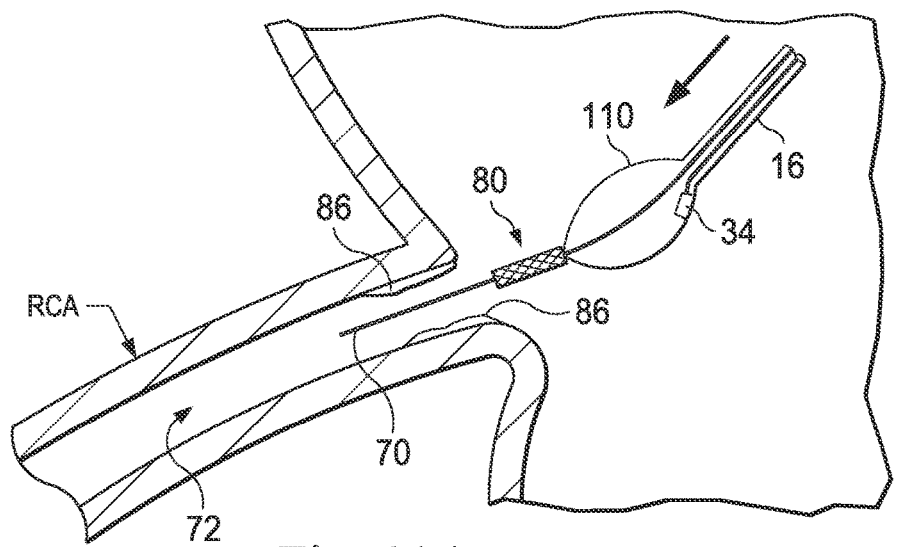
FIGS. 11A to 11E illustrate another variation where a stent may be positioned upon a balloon integrated with a visualization balloon positioned proximally of the stent for deployment within a vessel.

In another variation, FIGS. 11A to 11E show cross-sectional views of a deployment catheter 16 utilizing an inflatable visualization balloon assembly 110 which remains enclosed rather than an open hood 12. The stent assembly 80 may be utilized with the visualization balloon 110 and positioned either through a lumen defined through the visualization balloon 110 or distally upon balloon 82, which in this example may be coupled as a separate balloon or integrated with visualization balloon 110 as a single balloon assembly, as shown in FIG. 11A. Balloon 82 in this variation may comprise a thin, tube-like deployment balloon with stent 84 crimped around it and with the relatively larger transparent visualization balloon 110 positioned proximally. Imager 34 may be positioned within balloon 110 for imaging through the balloons 110 and/or 82 for visualizing the ostium OS as well as the vessel walls.

Figure 11B:
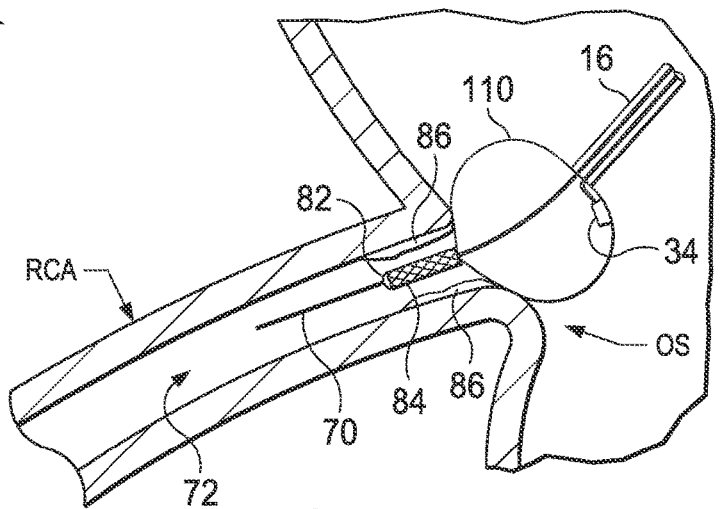

With guidewire 70 advanced through the lumen 72 of, e.g., right coronary artery RCA, stent 84 and balloon 82 maybe inserted at least partially into the right coronary artery RCA. The proximal visualization balloon 110 may be inflated and pushed distally until the balloon surface is firmly in contact with the vessel ostium OS and free from blood between the balloon-tissue interface to visualize the ostium OS, as shown in FIG. 11B. The positioning of the stent 84 with respect to the ostial lesion 86 can thus be viewed with imaging element 34 inside the visualization balloon 110. Stent 84 can then be manipulated by pushing or pulling the balloon system against the ostial lesion 86. With the inflated visualization balloon 110 firmly pressing against the ostium OS, the operator may also be able to ensure that the stent 84 is not placed too proximally such that parts of the stent 84 is not protruding into the aortic lumen which can cause thrombus or other complications.

Figure 11C:
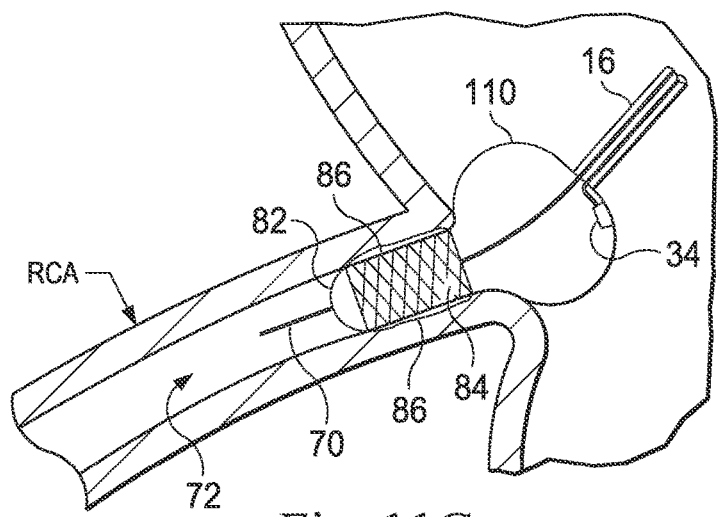
Figure 11D:
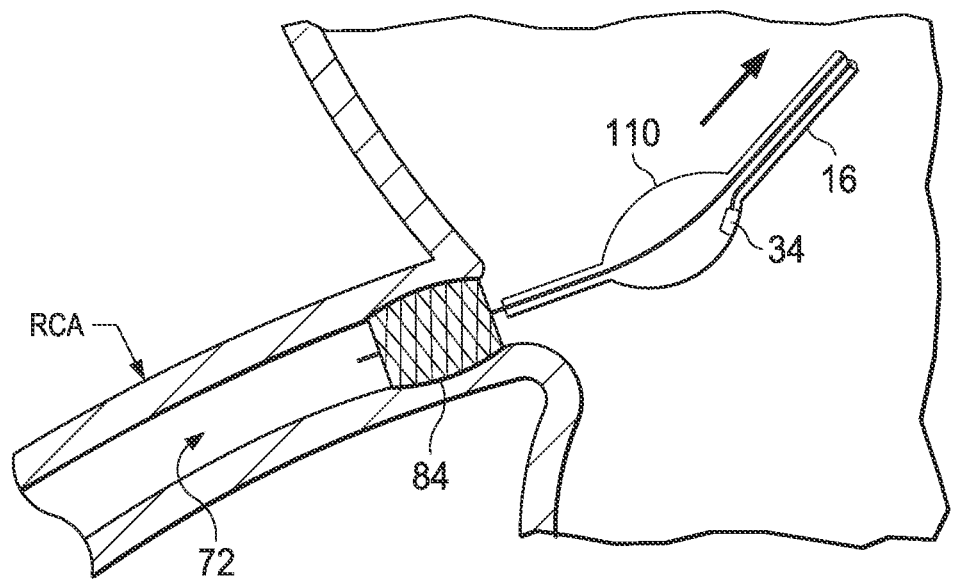
Figure 11E:
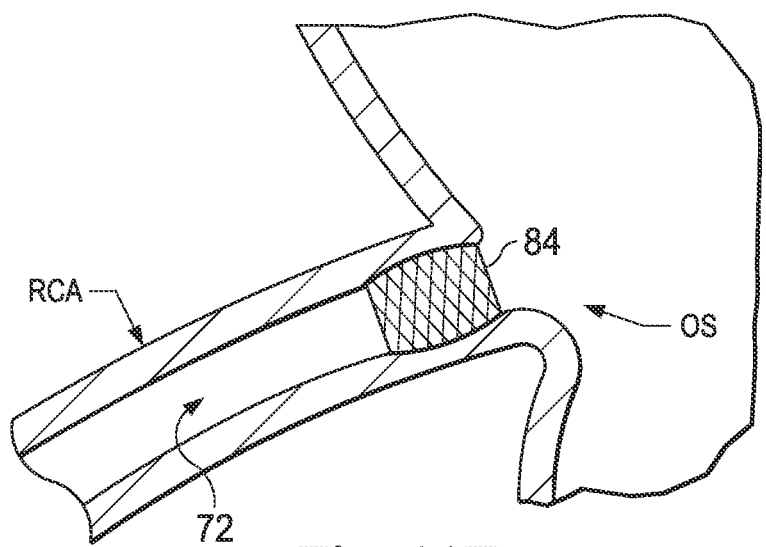

Upon visual confirmation that the stent 84 is positioned at its desired location and overlapping the ostial lesion 86, the deployment balloon 82 may be inflated until the stent 84 attains its stable configuration and is securely placed within the vessel, as shown in FIG. 11C, while the entire procedure is viewed under direct visualization with imaging element 34. Upon the successful placement of the stent 84 at the site of ostial lesion 86, one or both balloon 82 and/or visualization balloon 110 may be deflated and reduced to their original configuration and withdrawn, as shown in FIG. 11D. The assembly may then be withdrawn along with the guidewire 70 leaving behind the stent 84, as shown in FIG. 11E.

Figure 12A:
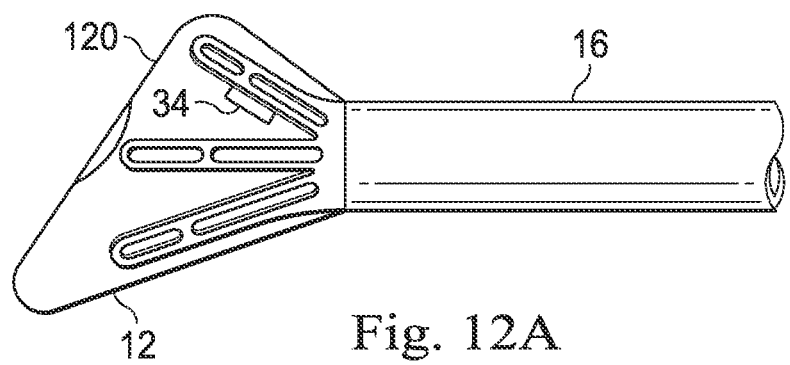
FIGS. 12A and 12B show a side view of a hood variation which utilizes an angled interface and the angled hood deployed within the body against an ostium.
Figure 12B:
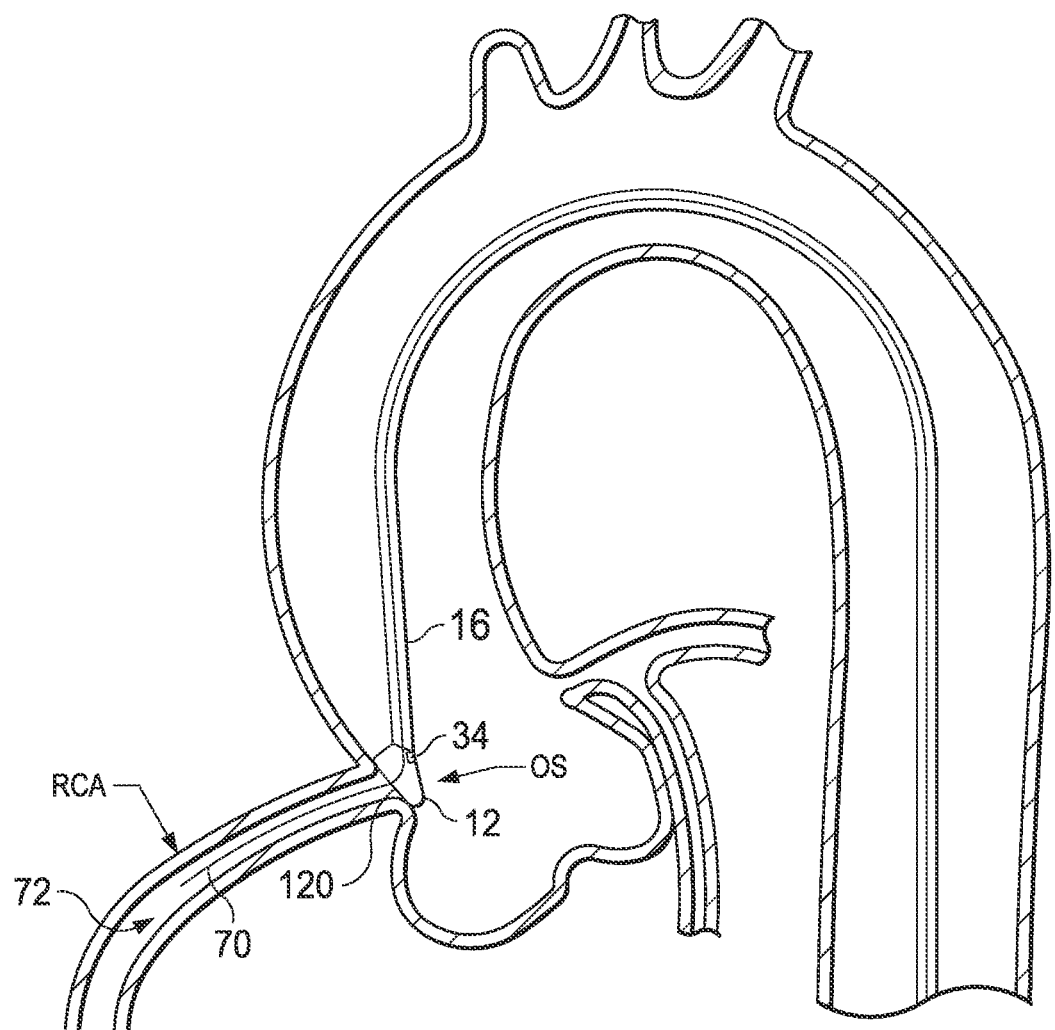

In yet another variation, FIG. 12A shows a side view of a deployment catheter 16 with hood 12 having an angled interface 120 which is angled relative to catheter 16. In this variation, an asymmetric, slanted hood 12 may be used to facilitate navigation within the aorta as the hood 12 may be better able to engage against a tissue region or ostium and establish visualization without the need to steer and/or articulate the catheter shaft perpendicularly within the narrow aorta lumen. As illustrated in FIG. 12B, angled interface 120 can be used to access the right coronary artery RCA without having to steer/articulate the deployment catheter 16 perpendicularly relative to ostium OS. A section of catheter 16 proximal to hood 12 can also optionally comprise a passive pre-shaped bend in place of an actively steerable section to assist the hood 12 in visualizing and accessing the coronary arteries.

The applications of the disclosed invention discussed above are not limited to certain treatments or regions of the body, but may include any number of other treatments and areas of the body. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A system, comprising:
   a deployment catheter having a lumen;
   a delivery sheath configured for positioning within the lumen of the deployment catheter; and
   a first measurement instrument configured for positioning within the delivery sheath, the first measurement instrument including a plurality of expandable members each having a known diameter in an expanded state, wherein the first measurement instrument is configured to determine a diameter of an anatomical lumen based on the known diameter of a most proximal expandable member that fits within the anatomical lumen.

2. The system of claim 1, wherein the plurality of expandable members are arranged in an order of increasing known diameter from a distal end of the plurality of expandable members to a proximal end of the plurality of expandable members.

3. The system of claim 1, further comprising an imaging element positioned to provide direct visualization of the first measurement instrument.

4. The system of claim 3, wherein the deployment catheter is configured to convey a fluid to purge bodily fluid from a volume between the imaging element and the first measurement instrument.

5. The system of claim 3, further comprising a second measurement instrument configured for positioning within the lumen, the second measurement instrument comprising a plurality of gradations spaced apart by known distances, wherein the imaging element is positioned to provide direct visualization of the second measurement instrument.

6. The system of claim 5, wherein the second measurement instrument is configured to be removed from the lumen prior to insertion of the first measurement instrument into the lumen.

7. The system of claim 5, wherein the second measurement instrument is configured to be advanced distally from the deployment catheter into the anatomical lumen to facilitate measurement of a length of a lesion based on direct visualization of the gradations and the lesion.

8. The system of claim 1, wherein the plurality of expandable members comprise one or more wire or mesh baskets.

9. The system of claim 1, wherein the plurality of expandable members comprise one or more distensible membranes.

10. The system of claim 1, wherein each of the plurality of expandable members includes a visual indication that distinguishes a respective expandable member from other expandable members of the plurality of expandable members.

11. The system of claim 10, wherein the visual indication comprises at least one of a color, a design, or a marking.

12. The system of claim 1, wherein the first measurement instrument is configured to be advanced distally from a distal end of the delivery sheath to expose the plurality of expandable members.

13. The system of claim 1, wherein the delivery sheath is configured to be retracted proximally to expose the plurality of expandable members.

14. The system of claim 1, wherein the plurality of expandable members have a delivery profile in which an unexpanded diameter of each of the plurality of expandable members is less than a diameter of a delivery lumen of the delivery sheath, wherein the known diameters of the plurality of expandable members in the expanded state are larger the diameter of the delivery lumen.

15. The system of claim 1, wherein the first measurement instrument is configured to be advanced distally from the deployment catheter into the anatomical lumen until one of the plurality of expandable members is blocked from insertion into the anatomical lumen.

16. The system of claim 15, wherein the known diameters of the plurality of expandable members correspond to stent sizes.

17. A method of measuring a lesion comprising:
positioning a deployment catheter with a lumen in proximity to an anatomical passageway in which the lesion is disposed;
advancing a first measurement instrument distally from the lumen, wherein the first measurement instrument includes a plurality of expandable members each having a known diameter in an expanded state, wherein the plurality of expandable members are arranged in an order of increasing known diameter from a distal end of the plurality of expandable members to a proximal end of the plurality of expandable members;
positioning at least one of the plurality of expandable members within the anatomical passageway;
imaging the first measurement instrument while the at least one of the plurality of expandable members is positioned within the anatomical passageway;
determining, based on the imaging, which expandable members of the plurality of expandable members fit within the anatomical passageway and which expandable members of the plurality of expandable members are obstructed from entry into the anatomical passageway; and
determining a diameter of the anatomical passageway based on the known diameter of a most proximal expandable member that fits within the anatomical passageway.

18. The method of claim 17, wherein the imaging comprises direct visualization with an imaging element disposed on the deployment catheter.

19. The method of claim 17, further comprising:
advancing, prior to or after advancing the first measurement instrument from the lumen, a second measurement instrument distally from the lumen;
directly visualizing the lesion and a plurality of gradations of the second measurement instrument, the plurality of gradations spaced apart by known distances; and
measuring a length of the lesion based on the direct visualization of the plurality of gradations.

* * * * *